(12) United States Patent
Kohno et al.

(10) Patent No.: US 7,232,559 B1
(45) Date of Patent: Jun. 19, 2007

(54) DIAGNOSTIC AGENTS FOR PANCREATIC EXOCRINE FUNCTION

(75) Inventors: Tadashi Kohno, Kanagawa (JP); Isaburo Hosoi, Saitama (JP); Junko Ohshima, Kanagawa (JP); Kunihiko Shibata, Chiba (JP); Asuka Ito, Kanagawa (JP)

(73) Assignee: Tokyo Gas Company Limited, Tokyo (JP)

( * ) Notice: Subject to any disclaimer, the term of this patent is extended or adjusted under 35 U.S.C. 154(b) by 0 days.

(21) Appl. No.: 09/453,642

(22) Filed: Dec. 3, 1999

Related U.S. Application Data

(63) Continuation-in-part of application No. 09/326,474, filed on Jun. 4, 1999.

(30) Foreign Application Priority Data

Nov. 15, 1999 (JP) .................................. 11/324128

(51) Int. Cl.
*A61K 51/00* (2006.01)
*A61M 36/14* (2006.01)

(52) U.S. Cl. .................. 424/1.81; 424/1.11; 424/1.65; 424/1.69; 424/9.1; 424/9.2

(58) Field of Classification Search ............... 424/1.11, 424/1.65, 1.69, 1.81, 9.1, 9.2; 530/300
See application file for complete search history.

(56) References Cited

U.S. PATENT DOCUMENTS

| | | | |
|---|---|---|---|
| 4,676,974 A | 6/1987 | Hofmann et al. | ............... 424/9 |
| 5,506,147 A | 4/1996 | Kolhouse et al. | ............. 436/86 |

FOREIGN PATENT DOCUMENTS

| | | |
|---|---|---|
| CA | 2273549 * | 12/1999 |
| EP | 0989137 A2 | 9/1999 |
| EP | 0966975 A2 | 12/1999 |
| EP | 1101499 A2 | 12/1999 |
| EP | 0989137 A2 | 3/2000 |
| EP | 99 304 388.4 | 5/2002 |
| JP | P99-0228 | 2/2002 |
| JP | P99-0228 | 5/2002 |
| WO | WO 80/01415 | 7/1980 |
| WO | WO 98/33531 | 8/1998 |
| WO | WO00/0636 | 1/2000 |

OTHER PUBLICATIONS

Rohrbach (Analytical Biochemistry, 1978, 84, 272-276).*
Fang et al ((Bioorganic & Medicinal Chemistry Letters, 1995, 5(22), 2701-2706).*
Xu et al (Biochemistry, 1997, 3, 14683-14689).*
Shiba K et al; "Comparative distribution study of 14C labeled amino acids, glucose-analogue and precursor of nuclei acid, as tumor seeking agents." Radioisotopes, (Aug. 1984) 33 (8) 526-32, XP000979062.
Takeda et al. "Biological Evaluation of Radiolabeled D-methionine as a Parent Compound in Potential Nuclear Imaging." Radioisotopes, (Apr. 1984) 33 (4) 231-7, XP001008478.
Tina S Morris et al., "In Vitro and Ex Vivo Inhibition of Hepatitis A Virus 3C Proteinase by a Peptidyl Monofluromethyl Ketone" *Bioorganic & Medicinal Chemistry*, vol. 5, No. 5, pp. 797-807.
Heller et al., "Solid-state NMR Studies of the Prion Protein H1 Fragment" *Protein Sci*. 5, 1655-61(1996), (abstract only).
Evenepoel P. et al., "Production of egg proteins, enriched with L-leucine-13C1, for the study of protein assimilation in humans using the breath test technique" *Human and Clinical Nutrition*, pp. 327-331.
Y. Ghoos, $CO_2$ Breath Tests at the laboratory "Digestion-Absorption", *University Hospital Gsthuisberg Lueven, Belguim*, pp. 94-96 (1996).
P. Evenepoel et al., "Egg Protein assimilation in pancreatic disease studied with a $^{13}C$-EGG white breath test", *Center for GI Research, University of Leuven*, pp. 99-100.
A. Takeda, et al., Biological Evaluation of Radiolabeled D-Methionine as Parent Compound in Potential Nuclear Imaging,, *Radioistopes*, pp. 213-217 (1984).
Daniel V Lim et al., "Purification and assay of bacterial collagenases", pp. 241-253 (1993).
Jonathan Heller et al., "Solid-state NMR studies of the prion protein H1 fragment", *Protein Science*; pp. 1655-1661 (1996).
Mitra et al "International Journal of Peptide and Protein Research" vol. 22, No. 4, pp. 501-508 (1983).
Thanabal et al "Journal of Biomolecular NMR", vol. 4, No. 1, pp. 46-59, (1994).
Serach Report.
"Time course of the total and radioactive carbon dioxide production by piglets receiving dietary [$^{14}C$]phenylalanine" by Ball et al., Department of Nutrition, University of Guelphe, Guelphe, Ont., Canada N1G 2W1, Received Sep. 20, 1984, Can. J. Physiol. Pharmacol. vol. 63, 1985, pp. 1170-1174.
Office Action from Canadian Intellectual Property Office dated Feb. 4, 2005.

* cited by examiner

*Primary Examiner*—Dameron L. Jones
(74) *Attorney, Agent, or Firm*—Finnegan, Henderson, Farabow, Garrett & Dunner LLP

(57) ABSTRACT

A diagnostic agent for pancreatic exocrine function comprising an amino acid or a peptide containing at least one $^{13}C$ or $^{14}C$ atom, or a pharmaceutically acceptable salt thereof other than Bz-Tyr-$^{13}C$-PABA is provided. A $^{13}C$- or $^{14}C$-labeled compound represented by the following formula (II):

$$X_2-R_2-Y_2-Z_1 \quad (II)$$

or a salt thereof,
wherein $X_2$ is a hydrogen atom or a protecting group,
$R_2$ is a peptide of 2 to 5 amino acids, an amino acid or a single bond,
$Y_2$ is an amino acid,
$Z_1$ is an amino acid optionally having a protecting group, and
at least one of the amino acids in $R_2$, $Y_2$ and $Z_1$, or at least one of the protecting groups in $X_2$ and $Z_1$ when the protecting groups contain a carbon atom, is $^{13}C$ or $^{14}C$-labeled.

42 Claims, 5 Drawing Sheets

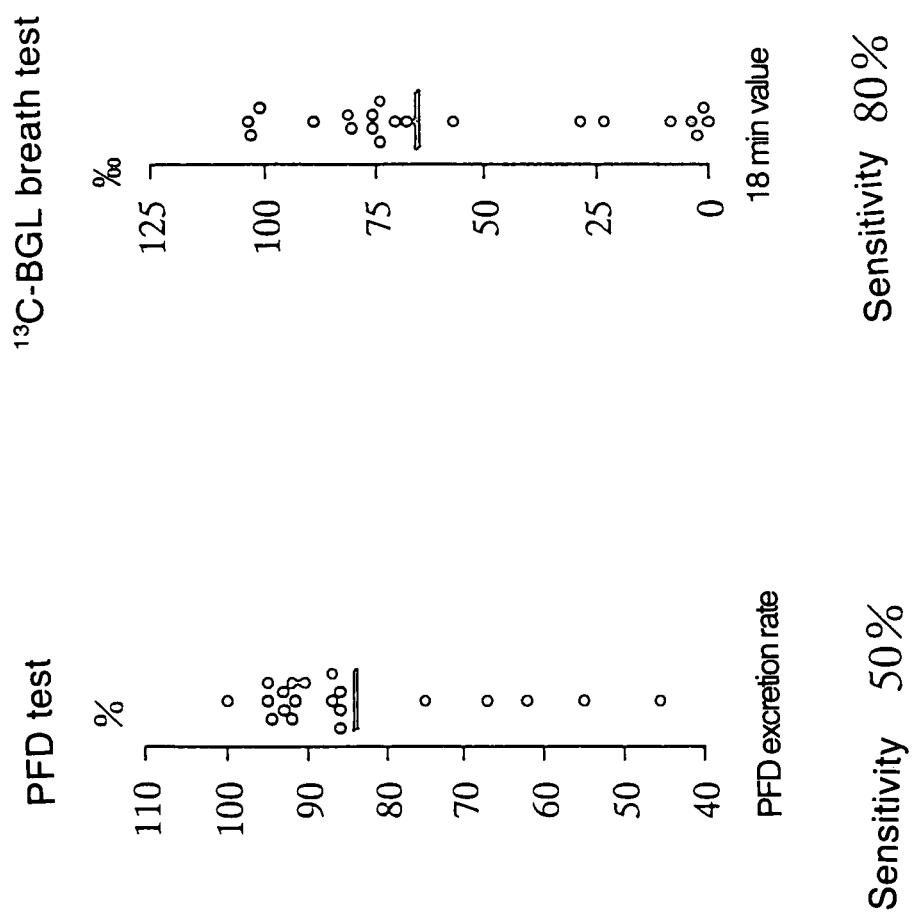

DIAGNOSTIC AGENTS FOR PANCREATIC EXOCRINE FUNCTION

CROSS-REFERENCES

This is a continuation-in-part of U.S. Ser. No. 09/326,474 with U.S. filing date of Jun. 4, 1999, which in turn claims the benefit of Japanese application serial numbers, 157855/1998 filed on Jun. 5, 1998 and 149496/1999 filed on May 28, 1999. The continuation-in-part also claims the benefit of Japanese application no. 324128/1999 filed on Nov. 15, 1999.

BACKGROUND OF THE INVENTION

1. Field of the Invention

The present invention relates to diagnostic agents for pancreatic exocrine function and novel compounds.

2. Background of the Invention

"Pancreatic exocrine function tests" are useful for the diagnosis of pancreatic diseases such as chronic and acute pancreatitis and pancreatic cancer. It is also useful to assess the condition and the prognosis of patients and to control the medication of protease preparations: The general descriptions are found in Arvanitakis and Cooke, Gastroenterology, 74:932 (1978); Niederau and Grendell, Gastroenterology, 88:1973 (1985); Goldberg, Bull. Mol. Biol. Med., 15:1 (1990); Lankisch, Int. J. Pancreatology, 14:9 (1993); Bank and Chow, Gastroenterologist, 2:224 (1994); and Steer et al., New Eng. J. Med., 332:1482 (1995).

The pancreatic exocrine function tests are roughly classified into intubation tests and tubeless tests. The intubation tests involve intubating a tube through the mouth to the duodenum to collect the duodenal juice. The secretin test is commonly used wherein secretin is intravenously administered to stimulate secretion of the pancreatic juice prior to the collection. This method is highly accurate since the amounts and components of the pancreatic juice are directly analyzed and is the "gold standard" of pancreatic exocrine function test. However, this method can not be used repeatedly or used for screening because of the very strong stress caused on the patients. It is not available at only a relatively small number of medical centers since the physician must be highly skilled. Further, since this method requires fluoroscopic tube placement during the collection of the duodenal juice, there is the problem of X ray exposure.

On the other hand, tubeless tests are easy to perform for estimating the pancreatic exocrine function which requires no intubation, wherein the excreted amount of compounds produced by pancreatic exocrine enzymes or the excreted amount of the pancreatic exocrine enzymes per se are measured. At present, the following four methods are mainly used:

1. PFD test wherein a synthetic substrate BT-PABA (N-benzoyl-L-tyrosyl-p-aminobenzoic acid) for chymotrypsin secreted from the pancreas is orally administered and the amount of PABA (p-aminobenzoic acid), a product degradated by chymotrypsin, excreted into the urine is measured;

2. PLT test wherein a synthetic substrate FDL (fluorescein dilaurate) for cholesterol ester hydrolase, esterase, secreted from the pancreas is orally administered and the amount of the degradation product fluorescein excreted into the urine or the concentration thereof in the blood is measured;

3. Fecal chymotrypsin test wherein chymotrypsin in the feces is quantitatively determined; and 4. Fecal elastase test wherein elastase in the feces is quantitatively determined.

However, the sensitivity any of these tests is too low to detect slight decreases of pancreatic exocrine function. Therefore, they have not been used that often in recent years.

To solve this problem, many easier pancreatic exocrine function tests have been searched for; $^{13}$C-breath tests have also been applied wherein a $^{13}$C-labeled compound is administered and an increase of the concentration of $^{13}CO_2$ in the exhalation is measured. Examples of such $^{13}$C-breath tests are illustrated below:

1. $^{13}$C-breath test wherein a $^{13}$C-labeled lipid or mixed triglyceride, which is a substrate for lipase, is administered: Chen et al., J. Nuclear Med., 15:1125 (1974); Watkins et al., J. Lab. Clin. Med., 90:422 (1977); Ghoos et al., Digestion, 22:239 (1981); John, S G., Gastroenterology, 83:44 (1982); Watkins et al., Gastroenterology, 82:911 (1982); Benini et al., Digestion, 29:91 (1984); Jones et al., J. Lab. Clin. Med., 105:647 (1985); Knoblach et al., Monatsschr Kinderheilkd, 136:26 (1988); Vantrappen et al., Gastroenterology, 96:1126 (1989); Murphy et al., Arch. Disease in Childhood, 65:574 (1990); Kato et al., Am. J. Gastroenterol., 88:64 (1993); McClean et al., Arch. Disease in Childhood, 69:366 (1993); Jakobs et al., Eur. J. Pediatr., 156:S78 (1997); and Kalivianakis et al., Eur. J. Clin. Invest., 27:434 (1997);

2. $^{13}$C-breath test wherein a $^{13}$C-labeled cholesterol ester, which is a substrate for cholesterol esterase, a lipase, is administered: Mundlos, et al., Pediatric Res., 22:257 (1987); Cole et al., Gastroenterology, 93:1372 (1987); and Mundlos et al., Gut, 31:1324 (1990);

3. $^{13}$C-breath test wherein a $^{13}$C-labeled starch, which is a substrate for an amylase, is administered: Hiele et al., Gastroenterology, 96:503 (1989); Dewit et al., Pediatric Res., 32:45 (1992); and Z. Gastroenterol., 35:187 (1997); and 4. $^{13}$C-breath test wherein a $^{13}$C-enriched egg protein, which is a protein having a $^{13}$C-concentration increased up to 1.4 atom % from the natural abundance of 1.1 atom % by feeding a chicken with $^{13}$C-leucine, and which is a substrate for a protease, is administered: Y. Ghoos, $^{13}CO_2$-Breath Tests at the laboratory "Digestion-Absorption", University Hospital Gasthuisberg, Leuven, Belgium (1996).

However, all these methods are less sensitive than the conventional ones and time-consuming. Therefore, these methods have not been established in clinical fields.

Thus, it is desirable that a highly sensitive pancreatic exocrine function test be developed that imparts low stress on the subject and give accurate results soon.

SUMMARY OF THE INVENTION

Accordingly, an object of the present invention is to provide a diagnostic agent for pancreatic exocrine function which leads to a highly sensitive test of pancreatic exocrine function imparting low stress on the subject and providing accurate results soon.

It is another object of the present invention to provide a novel compound for the pancreatic exocrine function test.

The present inventors have found that pancreatic exocrine function can be estimated with high sensitivity by orally administering a $^{13}$C-labeled peptide compound to a normal rat and a rat with chronic pancreatitis and measuring the $^{13}$C concentration in the exhaled $CO_2$ after administration. Thus, the present invention was completed.

The subject matters of the present inventions are as follows:

[1] A diagnostic agent for pancreatic exocrine function comprising an amino acid or a peptide containing at least one $^{13}C$ or $^{14}C$ atom, or a pharmaceutically acceptable salt thereof other than Bz-L-Tyr-$^{13}C$-PABA.

[2] The diagnostic agent of [1], wherein the amino acid molecule contains a $^{13}C$ or $^{14}C$ atom.

[3] The diagnostic agent of [1], wherein the amino acid or peptide has a modifying or protecting group and the modifying or protecting group contains a $^{13}C$ or $^{14}C$ atom.

[4] The diagnostic agent of any one of [1]–[3], wherein the amino acid or peptide is represented by the following formula (I):

$$X_1-R_1-Y_1 \quad (I)$$

wherein $X_1$ is a hydrogen atom or a protecting group, $R_1$ is a peptide of 2 to 50 amino acids, an amino acid or a single bond, $Y_1$ is an amino acid optionally having a protecting group.

[5] The diagnostic agent of [4], wherein at least one of the amino acids in $R_1$ and $Y_1$, or at least an ester group in $Y_1$ when the amino acid in $Y_1$ is protected with the ester group, is $^{13}C$- or $^{14}C$-labeled.

[6] The diagnostic agent of any one of [1]–[5], wherein after the reaction of a protease or proteases, the amino acid or peptide, or pharmaceutically acceptable salt thereof is decarboxylated to generate $^{13}CO_2$ or $^{14}CO_2'$

[7] The diagnostic agent of [6], wherein the protease or proteases are pancreatic exocrine proteases.

[8] The diagnostic agent of [7], wherein the pancreatic exocrine protease or proteases are selected from the group consisting of chymotrypsin, trypsin, elastase, and carboxypeptidases.

[9] The diagnostic agent of any one of [1]–[8], which is used in a breath test.

[10] A $^{13}C$- or $^{14}C$-labeled compound represented by the following formula (II):

$$X_2-R_2-Y_2-Z_1 \quad (II)$$

or a salt thereof, wherein $X_2$ is a hydrogen atom or a protecting group, $R_2$ is a peptide of 2 to 5 amino acids, an amino acid or a single bond, $Y_2$ is an amino acid, $Z_1$ is an amino acid optionally having a protecting group, and at least one of the amino acids in $R_2$, $Y_2$ and $Z_1$, or at least one of the protecting groups in $X_2$ and $Z_1$ when the protecting groups contain a carbon atom, is $^{13}C$- or $^{14}C$-labeled, provided that the following compounds are excluded:

L-Ala-L-Pro, L-Gly-L-Leu, L-Gly-L-Phe, L-Val-L-Leu, L-Leu-L-Leu, L-Tyr-L-Leu, Ac-D-Ala-D-Ala, L-Gly-L-Gly-OEt, L-Leu-L-Ala-OMe, Ac-L-Gly-L-Pro-OMe, Boc-L-Leu-L-Ala-OMe, L-Gly-L-Pro-L-Leu, L-Gly-L-Pro-L-Phe, L-Ala-L-Gly-L-Gly, L-Gly-L-Leu-L-Pro, L-Phe-L-Asp-L-Met, L-Gly-L-Leu-L-Pro, Dansyl-L-Tyr-L-Val-D-Ala, Cbz-L-Gly-L-Leu-L-Ala, L-Thr-L-Leu-L-Asn-Bzl, Z-L-Pro-L-Pro-L-Gly-OEt, L-Leu-L-Leu-L-Leu-L-Leu, L-Lys-L-Arg-L-Asp-L-Ser, Ac-L-Leu-L-Ala-L-Ala-L-Gln(NMe$_2$), Ac-L-Leu-L-Ala-L-Ala-L-Gln(NMe$_2$)-SEt, L-Tyr-L-Gly-L-Gly-L-Phe-L-Leu and L-Tyr-L-Gly-L-Gly-L-Phe-L-Met, wherein Ac is acetyl, Et is ethyl, Me is methyl, Boc is t-butyloxycarbonyl, Cbz is carbobenzyloxy, Bzl is benzoyl, Z is benzyloxycarbonyl, SEt is ethanethiol, and NMe$_2$ is dimethylamino.

[11] The $^{13}C$- or $^{14}C$-labeled compound, or salt thereof of [10], wherein 1) in the case where $X_2$ is a protecting group and $R_2$ is a single bond,
 1-i) when $Z_1$ is D-Ala, $Y_2$ is an amino acid other than D-Ala,
 1-ii) when $Z_1$ is L-Ala-OMe, $Y_2$ is an amino acid other than L-Leu,
 1-iii) when $Z_1$ is L-Pro-OMe, $Y_2$ is an amino acid other than L-Gly, 2) in the case where $X_2$ is a protecting group and $R_2$ is an amino acid,
 2-i) when $Z_1$ is D-Ala, $Y_2$ is an amino acid other than L-Val,
 2-ii) when $Z_1$ is L-Ala, $Y_2$ is an amino acid other than L-Leu,
 2-iii) when $Z_1$ is L-Gly-OEt, $Y_2$ is an amino acid other than L-Pro, 3) in the case where $X_2$ is a protecting group, $R_2$ is a peptide of 2 amino acids and $Z_1$ is L-Gln optionally having SEt, $Y_2$ is an amino acid other than L-Ala, 4) in the case where $X_2$ is a hydrogen atom and $R_2$ is a single bond,
 4-i) when $Z_1$ is L-Pro, $Y_2$ is an amino acid other than L-Ala,
 4-ii) when $Z_1$ is L-Leu, $Y_2$ is an amino acid other than L-Gly, L-Val, L-Leu and L-Tyr,
 4-iii) when $Z_1$ is L-Phe, $Y_2$ is an amino acid other than L-Gly,
 4-iv) when $Z_1$ is L-Gly-OEt, $Y_2$ is an amino acid other than L-Gly,
 4-v) when $Z_1$ is L-Ala-OMe, $Y_2$ is an amino acid other than L-Leu, 5) in the case where $X_2$ is a hydrogen atom and $R_2$ is an amino acid,
 5-i) when $Z_1$ is L-Leu, $Y_2$ is an amino acid other than L-Pro,
 5-ii) when $Z_1$ is L-Phe, $Y_2$ is an amino acid other than L-Pro,
 5-iii) when $Z_1$ is L-Gly, $Y_2$ is an amino acid other than L-Gly,
 5-iv) when $Z_1$ is L-Pro, $Y_2$ is an amino acid other than L-Leu,
 5-v) when $Z_1$ is L-Met, $Y_2$ is an amino acid other than L-Asp,
 5-vi) when $Z_1$ is L-Asn-Bzl, $Y_2$ is an amino acid other than L-Leu, 6) in the case where $X_2$ is a hydrogen atom and $R_2$ is a peptide of 2 amino acids,
 6-i) when $Z_1$ is L-Leu, $Y_2$ is an amino acid other than L-Leu,
 6-ii) when $Z_1$ is L-Ser, $Y_2$ is an amino acid other than L-Asp, and 7) in the case where $X_2$ is a hydrogen atom and $R_2$ is a peptide of 3 amino acids,
 7-i) when $Z_1$ is L-Leu, $Y_2$ is an amino acid other than L-Phe, 7-ii) when $Z_1$ is L-Met, $Y_2$ is an amino acid other than L-Phe.

[12] The $^{13}$C- or $^{14}$C-labeled compound, or salt thereof of [10] or [11], wherein 1) in the case where $X_2$ is a protecting group selected from the group consisting of Dansyl, Cbz, Ac and Z, and $R_2$ is an amino acid or a peptide of 2 amino acids,
   1-i) when $Z_1$ is D-Ala, $Y_2$ is an amino acid other than L-Val,
   1-ii) when $Z_1$ is L-Ala, $Y_2$ is an amino acid other than L-Leu,
   1-iii) when $Z_1$ is L-Gly-OEt, $Y_2$ is an amino acid other than L-Pro,
   1-iv) when $Z_1$ is L-Gln(NMe$_2$) or L-Gln(NMe$_2$)-SEt, $Y_2$ is an amino acid other than L-Ala, 2) in the case where $X_2$ is Ac or Boc, and $R_2$ is a single bond,
   2-i) when $Z_1$ is D-Ala, $Y_2$ is an amino acid other than D-Ala,
   2-ii) when $Z_1$ is L-Pro-OMe, $Y_2$ is an amino acid other than L-Gly,
   2-iii) when $Z_1$ is L-Ala-OMe, $Y_2$ is an amino acid other than L-Leu, 3) in the case where $X_2$ is a hydrogen atom and $R_2$ is an amino acid or a peptide of 2 or 3 amino acids,
   3-i) when $Z_1$ is L-Leu, $Y_2$ is an amino acid other than L-Pro, L-Leu and L-Phe,
   3-ii) when $Z_1$ is L-Phe, $Y_2$ is an amino acid other than L-Pro,
   3-iii) when $Z_1$ is L-Gly, $Y_2$ is an amino acid other than L-Gly,
   3-iv) when $Z_1$ is L-Pro, $Y_2$ is an amino acid other than L-Leu,
   3-v) when $Z_1$ is L-Met, $Y_2$ is an amino acid other than L-Asp and L-Phe,
   3-vi) when $Z_1$ is L-Asn-Bzl, $Y_2$ is an amino acid other than L-Leu,
   3-vii) when $Z_1$ is L-Ser, $Y_2$ is an amino acid other than L-Asp, and 4) in the case where $X_2$ is a hydrogen atom and $R_2$ is a single bond,
   4-i) when $Z_1$ is L-Pro, $Y_2$ is an amino acid other than L-Ala,
   4-ii) when $Z_1$ is L-Leu, $Y_2$ is an amino acid other than L-Gly, L-Val, L-Leu and L-Tyr,
   4-iii) when $Z_1$ is L-Phe, $Y_2$ is an amino acid other than L-Gly,
   4-iv) when $Z_1$ is L-Gly-OEt, $Y_2$ is an amino acid other than L-Gly,
   4-v) when $Z_1$ is L-Ala-OMe, $Y_2$ is an amino acid other than L-Leu.

[13] The $^{13}$C- or $^{14}$C-labeled compound or salt thereof of any one of [10]–[12], wherein $X_2$ is selected from the group consisting of Ac, Bz (benzoyl), Boc, Z and a hydrogen atom.

[14] The $^{13}$C- or $^{14}$C-labeled compound or salt thereof of any one of [10]–[13], wherein after the reaction of a protease or proteases, the amino acid or peptide, or salt thereof is decarboxylated to generate $^{13}CO_2$ or $^{14}CO_2$.

[15] The $^{13}$C- or $^{14}$C-labeled compound or salt thereof of [14], wherein the protease or proteases are pancreatic exocrine proteases.

[16] The $^{13}$C- or $^{14}$C-labeled compound or salt thereof of [15], wherein the pancreatic exocrine protease or proteases are selected from the group consisting of chymotrypsin, trypsin, elastase, and carboxypeptidases.

[17] The $^{13}$C- or $^{14}$C-labeled compound or salt thereof of any one of [10]–[16], wherein $X_2$ is a protecting group and $R_2$ is a single bond.

[18] The $^{13}$C- or $^{14}$C-labeled compound or salt thereof of any one of [10]–[17], wherein (1) at least one of the amino acids in $Y_2$ and $Z_1$ is Arg or Lys, (2) at least one of the amino acids in $Y_2$ and $Z_1$ is an aromatic amino acid, Leu, His or Met, (3) at least one of the amino acids in $Y_2$ and $Z_1$ is a neutral and non-aromatic amino acid, (4) the amino acid in $Z_1$ is an amino acid other than Arg, Lys and Pro, or (5) the amino acid in $Z_1$ is Arg or Lys.

[19] The $^{13}$C- or $^{14}$C-labeled compound or salt thereof of any one of [10]–[18], wherein $X_2$ is selected from the group consisting of a hydrogen atom, Bz, Ac and Boc, $Y_2$ is selected from the group consisting of Phe, Ala, Gly, Tyr and Arg, and $Z_1$ is selected from the group consisting of Leu optionally having a protecting group, Ala optionally having a protecting group, and Gly optionally having a protecting group.

[20] The $^{13}$C- or $^{14}$C-labeled compound or salt thereof of [19], wherein $Z_1$ is selected from the group consisting of Leu, Ala, Gly, Leu-OMe, Leu-OEt, Ala-OMe, Ala-OEt, Gly-OMe and Gly-OEt.

[21] The $^{13}$C- or $^{14}$C-labeled compound or salt thereof of any one of [10]–[20], wherein $Z_1$ is a $^{13}$C- or $^{14}$C-labeled amino acid optionally having a protecting group.

[22] The $^{13}$C- or $^{14}$C-labeled compound or salt thereof of [10], which is selected from the group consisting of the following compounds:

(a) Phe-$^{13}$C-Leu, (b) Arg-$^{13}$C-Leu, (c) Bz-Ala-$^{13}$C-Ala, (d) Bz-Gly-$^{13}$C-Leu, (e) Bz-Phe-$^{13}$C-Gly, (f) Bz-Tyr-$^{13}$C-Leu, (g) Bz-Phe-$^{13}$C-Leu, (h) Bz-(DL)Phe-$^{13}$C-Leu, (j) Bz-Arg-$^{13}$C-Leu, (k) Ac-Phe-$^{13}$C-Leu, (l) Ac-Tyr-$^{13}$C-Leu, (m) Bz-Ala-$^{13}$C-Ala-OMe, (n) Bz-Gly-$^{13}$C-Leu-OMe, (o) Bz-Phe-$^{13}$C-Gly-OMe, (p) Bz-Phe-$^{13}$C-Leu-OMe, (q) Bz-(DL)Phe-$^{13}$C-Leu-OMe, (r) Ac-Phe-$^{13}$C-Leu-OMe, (s) Ac-Tyr-$^{13}$C-Leu-OMe, (t) Bz-Ala-Ala-Ala-Ala-Gly-Phe-$^{13}$C-Leu, (u) Boc-Ala-Ala-Ala-Ala-Gly-Phe-$^{13}$C-Leu, and (v) Bz-Ala-Ala-Ala-Ala-$^{13}$C-Gly-Phe-Leu.

[23] A diagnostic agent for pancreatic exocrine function comprising an amino acid or a peptide containing at least one $^{13}$C or $^{13}$C atom, or a pharmaceutically acceptable salt thereof other than Bz-L-Tyr-$^{13}$C-PABA, wherein said amino acid or all amino acids constituting said peptide is (are) an L-isomer(s).

[24] The diagnostic agent of [23], wherein the amino acid molecule contains a $^{13}$C or $^{14}$C atom.

[25] The diagnostic agent of [23], wherein the amino acid or peptide has a modifying or protecting group and the modifying or protecting group contains a $^{13}$C or $^{14}$C atom.

[26] The diagnostic agent of any one of [23]—[25], wherein the amino acid or peptide is represented by the following formula (I):

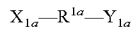  (Ia)

wherein $X_{1a}$ is a hydrogen atom or a protecting group, $R_{1a}$ is a peptide of 2 to 50 amino acids, an amino acid or a single bond, $Y_{1a}$ is an amino acid optionally having a protecting group.

[27] The diagnostic agent of [26], wherein at least one of the amino acids in $R_{1a}$ and $Y_{1a}$, or at least an ester group in $Y_{1a}$ when the amino acid in $Y_{1a}$ is protected with the ester group, is $^{13}$C- or $^{14}$C-labeled.

[28] The diagnostic agent of any one of [23]—[27], wherein after the reaction of a protease or proteases, the amino acid or peptide, or pharmaceutically acceptable salt thereof is decarboxylated to generate $^{13}CO_2$ or $^{14}CO_2$.

[29] The diagnostic agent of [28], wherein the protease or proteases are pancreatic exocrine proteases.

[30] The diagnostic agent of [29], wherein the pancreatic exocrine protease or proteases are selected from the group consisting of chymotrypsin, trypsin, elastase, and carboxypeptidases.

[31] The diagnostic agent of any one of [23]–[30], which is used in a breath test.

[32] A $^{13}$C- or $^{14}$C-labeled compound represented by the following formula (IIa):

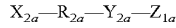  (IIa)

or a salt thereof, wherein all amino acids constituting the labeled compound are L-isomers, wherein $X_{2a}$ is a hydrogen atom or a protecting group, $R_{2a}$ is a peptide of 2 to 5 amino acids, an amino acid or a single bond, $Y_{2a}$ is an amino acid, $Z_{1a}$ is an amino acid optionally having a protecting group, and at least one of the amino acids in $R_{2a}$, $Y_{2a}$ and $Z_{1a}$, or at least one of the protecting groups in $X_{2a}$ and $Z_{1a}$ when the protecting groups contain a carbon atom, is $^{13}$C- or $^{14}$C-labeled, provided that the following compounds are excluded from the compounds represented by the formula (IIa)

L-Ala-L-Pro, L-Gly-L-Leu, L-Gly-L-Phe, L-Val-L-Leu, L-Leu-L-Leu, L-Tyr-L-Leu, L-Gly-L-Gly-OEt, L-Leu-L-Ala-OMe, Ac-L-Gly-L-Pro-OMe, Boc-L-Leu-L-Ala-OMe, L-Gly-L-Pro-L-Leu, L-Gly-L-Pro-L-Phe, L-Ala-L-Gly-L-Gly, L-Gly-L-Leu-L-Pro, L-Phe-L-Asp-L-Met, L-Gly-L-Leu-L-Pro, Cbz-L-Gly-L-Leu-L-Ala, L-Thr-L-Leu-L-Asn-Bzl, Z-L-Pro-L-Pro-L-Gly-OEt, L-Leu-L-Leu-L-Leu-L-Leu, L-Lys-L-Arg-L-Asp-L-Ser, Ac-L-Leu-L-Ala-L-Ala-L-Gln(NMe$_2$), Ac-L-Leu-L-Ala-L-Ala-L-Gln(NMe$_2$)-SEt, L-Tyr-L-Gly-L-Gly-L-Phe-L-Leu and L-Tyr-L-Gly-L-Gly-L-Phe-L-Met, wherein Ac is acetyl, Et is ethyl, Me is methyl, Boc is t-butyloxycarbonyl, Cbz is carbobenzyloxy, Bzl is benzoyl, Z is benzyloxycarbonyl, SEt is ethanethiol, and NMe$_2$ is dimethylamino.

[33] The $^{13}$C- or $^{14}$C-labeled compound, or salt thereof of [32], wherein 1) in the case where $X_{2a}$ is a protecting group and $R_{2a}$ is a single bond, 1-i) when $Z_{1a}$ is L-Ala-OMe, $Y_{2a}$ is an amino acid other than L-Leu, 1-ii) when $Z_{1a}$ is L-Pro-OMe, $Y_{2a}$ is an amino acid other than L-Gly, 2) in the case where $X_{1a}$ is a protecting group and $R_{2a}$ is an amino acid, 2-i) when $Z_{1a}$ is L-Ala, $Y_{2a}$ is an amino acid other than L-Leu, 2-ii) when $Z_{1a}$ is L-Gly-OEt, $Y_{2a}$ is an amino acid other than L-Pro, 3) in the case where $X_{2a}$ is a protecting group, $R_{2a}$ is a peptide of 2 amino acids and $Z_{1a}$ is L-Gln optionally having SEt, $Y_{2a}$ is an amino acid other than L-Ala, 4) in the case where $X_{2a}$ is a hydrogen atom and $R_{2a}$ is a single bond, 4-i) when $Z_{1a}$ is L-Pro, $Y_{2a}$ is an amino acid other than L-Ala, 4-ii) when $Z_{1a}$ is L-Leu, $Y_{2a}$ is an amino acid other than L-Gly, L-Val, L-Leu and L-Tyr, 4-iii) when $Z_{1a}$ is L-Phe, $Y_{2a}$ is an amino acid other than L-Gly, 4-iv) when $Z_{1a}$ is L-Gly-OEt, $Y_{2a}$ is an amino acid other than L-Gly, 4-v) when $Z_{1a}$ is L-Ala-OMe, $Y_{2a}$ is an amino acid other than L-Leu, 5) in the case where $X_{2a}$ is a hydrogen atom and $R_{2a}$ is an amino acid, 5-i) when $Z_{1a}$ is L-Leu, $Y_{2a}$ is an amino acid other than L-Pro, 5-ii) when $Z_{1a}$ is L-Phe, $Y_{2a}$ is an amino acid other than L-Pro, 5-iii) when $Z_{1a}$ is L-Gly, $Y_{2a}$ is an amino acid other than L-Gly, 5-iv) when $Z_{1a}$ is L-Pro, $Y_{2a}$ is an amino acid other than L-Leu, 5-v) when $Z_{1a}$ is L-Met, $Y_{2a}$ is an amino acid other than L-Asp, 5-vi) when $Z_{1a}$ is L-Asn-Bzl, $Y_{2a}$ is an amino acid other than L-Leu, 6) in the case where $X_{2a}$ is a hydrogen atom and $R_{2a}$ is a peptide of 2 amino acids, 6-i) when $Z_{1a}$ is L-Leu, $Y_{2a}$ is an amino acid other than L-Leu, 6-ii) when $Z_{1a}$ is L-Ser, $Y_{2a}$ is an amino acid other than L-Asp, and 7) in the case where $X_{2a}$ is a hydrogen atom and $R_{2a}$ is a peptide of 3 amino acids, 7-i) when $Z_{1a}$ is L-Leu, $Y_{2a}$ is an amino acid other than L-Phe, 7-i) when $Z_{1a}$ is L-Met, $Y_{2a}$ is an amino acid other than L-Phe.

[34] The $^{13}$C- or $^{14}$C-labeled compound, or salt thereof of [32] or [33], wherein 1) in the case where $X_{2a}$ is a protecting group selected from the group consisting of Cbz, Ac and Z, and $R_{2a}$ is an amino acid or a peptide of 2 amino acids,
    1-i) when $Z_{1a}$ is L-Ala, $Y_{2a}$ is an amino acid other than L-Leu,
    1-ii) when $Z_{1a}$ is L-Gly-OEt, $Y_{2a}$ is an amino acid other than L-Pro,
    1-iii) when $Z_{1a}$ is L-Gln(NMe$_2$) or L-Gln(NMe$_2$)-SEt, $Y_{2a}$ is an amino acid other than L-Ala, 2) in the case where $X_{2a}$ is Ac or Boc, and $R_{2a}$ is a single bond,
    2-i) when $Z_{1a}$ is L-Pro-OMe, $Y_{2a}$ is an amino acid other than L-Gly,
    2-ii) when $Z_{1a}$ is L-Ala-OMe, $Y_{2a}$ is an amino acid other than L-Leu, 3) in the case where $X_{2a}$ is a hydrogen atom and $R_{2a}$ is an amino acid or a peptide of 2 or 3 amino acids,
    3-i) when $Z_{1a}$ is L-Leu, $Y_{2a}$ is an amino acid other than L-Pro, L-Leu and L-Phe,
    3-ii) when $Z_{1a}$ is L-Phe, $Y_{2a}$ is an amino acid other than L-Pro,
    3-iii) when $Z_{1a}$ is L-Gly, $Y_{2a}$ is an amino acid other than L-Gly,
    3-iv) when $Z_{1a}$ is L-Pro, $Y_{2a}$ is an amino acid other than L-Leu,
    3-v) when $Z_{1a}$ is L-Met, $Y_{2a}$ is an amino acid other than L-Asp and L-Phe,
    3-vi) when $Z_{1a}$ is L-Asn-Bzl, $Y_{2a}$ is an amino acid other than L-Leu,
    3-vii) when $Z_{1a}$ is L-Ser, $Y_{2a}$ is an amino acid other than L-Asp, and 4) in the case where $X_{2a}$ is a hydrogen atom and $R_{2a}$ is a single bond,
    4-i) when $Z_{1a}$ is L-Pro, $Y_{2a}$ is an amino acid other than L-Ala,
    4-ii) when $Z_{1a}$ is L-Leu, $Y_{2a}$ is an amino acid other than L-Gly, L-Val, L-Leu and L-Tyr,
    4-iii) when $Z_{1a}$ is L-Phe, $Y_{2a}$ is an amino acid other than L-Gly,
    4-iv) when $Z_{1a}$ is L-Gly-OEt, $Y_{2a}$ is an amino acid other than L-Gly,
    4-v) when $Z_{1a}$ is L-Ala-OMe, $Y_{2a}$ is an amino acid other than L-Leu.

[35] The $^{13}$C- or $^{14}$C-labeled compound or salt thereof of any one of [32]–[34], wherein $X_{2a}$ is selected from the group consisting of Ac, Bz (benzoyl), Boc, Z and a hydrogen atom.

[36] The $^{13}$C- or $^{14}$C-labeled compound or salt thereof of any one of [32]–[35], wherein after the reaction of a protease or proteases, the amino acid or peptide, or salt thereof is decarboxylated to generate $^{13}CO_2$ or $^{14}CO_2$.

[37] The $^{13}$C- or $^{14}$C-labeled compound or salt thereof of [36], wherein the protease or proteases are pancreatic exocrine proteases.

[38] The $^{13}$C- or $^{14}$C-labeled compound or salt thereof of [37], wherein the pancreatic exocrine protease or proteases are selected from the group consisting of chymotrypsin, trypsin, elastase, and carboxypeptidases.

[39] The $^{13}$C- or $^{14}$C-labeled compound or salt thereof of any one of [32]–[38] wherein $X_{2a}$ is a protecting group and $R_{2a}$ is a single bond.

[40] The $^{13}$C- or $^{14}$C-labeled compound or salt thereof of any one of [32]–[39], wherein (1) at least one of the amino acids in $Y_{2a}$ and $Z_{1a}$ is L-Arg or L-Lys, (2) at least one of the amino acids in $Y_{2a}$ and $Z_{1a}$ is an aromatic L-amino acid, L-Leu, L-His or L-Met, (3) at least one of the amino acids in $Y_{2a}$ and $Z_{1a}$ is a neutral and non-aromatic L-amino acid, (4) the amino acid in $Z_{1a}$ is an L-amino acid other than L-Arg, L-Lys and L-Pro, or (5) the amino acid in $Z_{1a}$ is L-Arg or L-Lys.

[41] The $^{13}$C- or $^{14}$C-labeled compound or salt thereof of any one of [32]–[40], wherein $X_{2a}$ is selected from the group consisting of a hydrogen atom, Bz, Ac and Boc, $Y_{2a}$ is selected from the group consisting of L-Phe, L-Ala, L-Gly, L-Tyr and L-Arg, and $Z_{1a}$ is selected from the group consisting of L-Leu optionally having a protecting group, L-Ala optionally having a protecting group, and L-Gly optionally having a protecting group.

[42] The $^{13}$C- or $^{14}$C-labeled compound or salt thereof of [41], wherein $Z_{1a}$ is selected from the group consisting of L-Leu, L-Ala, L-Gly, L-Leu-OMe, L-Leu-OEt, L-Ala-OMe, L-Ala-OEt, L-Gly-OMe and L-Gly-OEt.

[43] The $^{13}$C- or $^{14}$C-labeled compound or salt thereof of any one of [32]–[42], wherein $Z_{1a}$ is a $^{13}$C- or $^{14}$C-labeled amino acid optionally having a protecting group.

[44] The $^{13}$C- or $^{14}$C-labeled compound or salt thereof of [32], which is selected from the group consisting of the following compounds:

(a) L-Phe-$^{13}$C-L-Leu, (b) L-Arg-$^{13}$C-L-Leu, (c) Bz-L-Ala-$^{13}$C-L-Ala, (d) Bz-L-Gly-$^{13}$C-L-Leu, (e) Bz-L-Phe-$^{13}$C-L-Gly, (f) Bz-L-Tyr-$^{13}$C-L-Leu, (g) Bz-L-Phe-$^{13}$C-L-Leu, (h) Bz-L-Arg-$^{13}$C-L-Leu, (i) Ac-L-Phe-$^{13}$C-L-Leu, (j) Ac-L-Tyr-$^{13}$C-L-Leu, (k) Bz-L-Ala-$^{13}$C-L-Ala-OMe, (l) Bz-L-Gly-$^{13}$C-L-Leu-OMe, (m) Bz-L-Phe-$^{13}$C-L-Gly-OMe, (n) Bz-L-Phe-$^{13}$C-L-Leu-OMe, (o) Ac-L-Phe-$^{13}$C-L-Leu-OMe, (p) Ac-L-Tyr-$^{13}$C-L-Leu-OMe, (q) Bz-L-Ala-L-Ala-L-Ala-L-Ala-L-Gly-L-Phe-$^{13}$C-L-Leu, (r) Boc-L-Ala-L-Ala-L-Ala-L-Ala-L-Gly-L-Phe-$^{13}$C-L-Leu, and (s) Bz-L-Ala-L-Ala-L-Ala-L-Ala-$^{13}$C-L-Gly-L-Phe-L-Leu.

[45] A diagnostic agent for pancreatic exocrine function comprising an amino acid or a peptide containing at least one $^{13}$C or $^{14}$C atom, or a pharmaceutically acceptable salt thereof, wherein at least one of said amino acid or amino acids constituting said peptide is a D-isomer or a DL-mixture.

[46] The diagnostic agent of [45], wherein the amino acid molecule contains a $^{13}$C or $^{14}$C atom.

[47] The diagnostic agent of [45], wherein the amino acid or peptide has a modifying or protecting group and the modifying or protecting group contains a $^{13}$C or $^{14}$C atom.

[48] The diagnostic agent of any one of [45]–[47], wherein the amino acid or peptide is represented by the following formula (I):

$$X_{1b}\text{—}R_{1b}\text{—}Y_{1b} \qquad (Ib)$$

wherein $X_{1b}$ is a hydrogen atom or a protecting group, $R_{1b}$ is a peptide of 2 to 50 amino acids, an amino acid or a single bond, $Y_{1b}$ is an amino acid optionally having a protecting group.

[49] The diagnostic agent of [48], wherein at least one of the amino acids in $R_{1b}$ and $Y_{1b}$, or at least an ester group in $Y_{1b}$ when the amino acid in $Y_{1b}$ is protected with the ester group, is $^{13}$C- or $^{14}$C-labeled.

[50] The diagnostic agent of any one of [45]–[49], wherein after the reaction of a protease or proteases, the amino acid or peptide, or pharmaceutically acceptable salt thereof is decarboxylated to generate $^{13}CO_2$ or $^{14}CO_2$.

[51] The diagnostic agent of [50], wherein the protease or proteases are pancreatic exocrine proteases.

[52] The diagnostic agent of [51], wherein the pancreatic exocrine protease or proteases are selected from the group consisting of chymotrypsin, trypsin, elastase, and carboxypeptidases.

[53] The diagnostic agent of any one of [45]–[52], which is used in a breath test.

[54] A $^{13}$C- or $^{14}$C-labeled compound represented by the following formula (IIb):

$$X_{2b}\text{—}R_{2b}\text{—}Y_{2b}\text{—}Z_{1b} \qquad (IIb)$$

or a salt thereof, wherein at least one of amino acids constituting the labeled compound is a D-isomer or a DL-mixture, wherein $X_{2b}$ is a hydrogen atom or a protecting group, $R_{2b}$ is a peptide of 2 to 5 amino acids, an amino acid or a single bond, $Y_{2b}$ is an amino acid, $Z_{1b}$ is an amino acid optionally having a protecting group, and at least one of the amino acids in $R_{2b}$, $Y_{2b}$ and $Z_{1b}$, or at least one of the protecting groups in $X_{2b}$ and $Z_{1b}$ when the protecting groups contain a carbon atom, is $^{13}$C- or $^{14}$C-labeled, provided that the following compounds are excluded from the compounds represented by the formula (IIb):

Ac-D-Ala-D-Ala and Dansyl-L-Tyr-L-Val-D-Ala, wherein Ac is acetyl.

[55] The $^{13}$C- or $^{14}$C-labeled compound, or salt thereof of [54], wherein 1) in the case where $X_{2b}$ is a protecting group and $R_{2b}$ is a single bond, when $Z_{1b}$ is D-Ala, $Y_{2b}$ is an amino acid other than D-Ala, 2) in the case where $X_{2b}$ is a protecting group and $R_{2b}$ is an amino acid, when $Z_{1b}$ is D-Ala, $Y_{2b}$ is an amino acid other than Val.

[56] The $^{13}$C- or $^{14}$C-labeled compound or salt thereof of any one of [54]–[55], wherein $X_{2b}$ is selected from the group consisting of Ac, Bz (benzoyl), Boc, Z and a hydrogen atom.

[57] The $^{13}$C- or $^{14}$C-labeled compound or salt thereof of any one of [54]–[56], wherein after the reaction of a protease or proteases, the amino acid or peptide, or salt thereof is decarboxylated to generate $^{13}CO_2$ or $^{14}CO_2$.

[58] The $^{13}$C- or $^{14}$C-labeled compound or salt thereof of [57], wherein the protease or proteases are pancreatic exocrine proteases.

[59] The $^{13}$C- or $^{14}$C-labeled compound or salt thereof of [58], wherein the pancreatic exocrine protease or proteases are selected from the group consisting of chymotrypsin, trypsin, elastase, and carboxypeptidases.

[60] The $^{13}$C- or $^{14}$C-labeled compound or salt thereof of any one of [54]–[59], wherein $X_{2b}$ is a protecting group and $R_{2b}$ is a single bond.

[61] The $^{13}$C- or $^{14}$C-labeled compound or salt thereof of any one of [54]–[60], wherein (1) at least one of the amino acids in $Y_{2b}$ and $Z_{1b}$ is Arg or Lys, (2) at least one of the amino acids in $Y_{2b}$ and $Z_{1b}$ is an aromatic amino acid, Leu, His or Met, (3) at least one of the amino acids in $Y_{2b}$ and $Z_{1b}$ is a neutral and non-aromatic amino acid, (4) the amino acid in $Z_{1b}$ is an amino acid other than Arg, Lys and Pro, or (5) the amino acid in $Z_{1b}$ is Arg or Lys.

[62] The $^{13}$C- or $^{14}$C-labeled compound or salt thereof of any one of [54]–[61], wherein $X_{2b}$ is selected from the group consisting of a hydrogen atom, Bz, Ac and Boc, $Y_{2b}$ is selected from the group consisting of Phe, Ala, Gly, Tyr and Arg, and $Z_{1b}$ is selected from the group consisting of Leu optionally having a protecting group, Ala optionally having a protecting group, and Gly optionally having a protecting group.

[63] The $^{13}$C- or $^{14}$C-labeled compound or salt thereof of [62], wherein $Z_{1b}$ is selected from the group consisting of Leu, Ala, Gly, Leu-OMe, Leu-OEt, Ala-OMe, Ala-OEt, Gly-OMe and Gly-OEt.

[64] The $^{13}$C- or $^{14}$C-labeled compound or salt thereof of any one of [54]–[63], wherein $Z_{1b}$ is a $^{13}$C- or $^{14}$C-labeled amino acid optionally having a protecting group.

[65] The $^{13}$C- or $^{14}$C-labeled compound or salt thereof of [54], which is selected from the group consisting of the following compounds:

(a) Phe-$^{13}$C-Leu, (b) Arg-$^{13}$C-Leu, (c) Bz-Ala-$^{13}$C-Ala, (d) Bz-Gly-$^{13}$C-Leu, (e) Bz-Phe-$^{13}$C-Gly, (f) Bz-Tyr-$^{13}$C-Leu, (g) Bz-Phe-$^{13}$C-Leu, (h) Bz-(DL)Phe-$^{13}$C-Leu, (j) Bz-Arg-$^{13}$C-Leu, (k) Ac-Phe-$^{13}$C-Leu, (l) Ac-Tyr-$^{13}$C-Leu, (m) Bz-Ala-$^{13}$C-Ala-OMe, (n) Bz-Gly-$^{13}$C-Leu-OMe, (o) Bz-Phe-$^{13}$C-Gly-OMe, (p) Bz-Phe-$^{13}$C-Leu-OMe, (q) Bz-(DL)Phe-$^{13}$C-Leu-OMe, (r) Ac-Phe-$^{13}$C-Leu-OMe, (s) Ac-Tyr-$^{13}$C-Leu-OMe, (t) Bz-Ala-Ala-Ala-Ala-Gly-Phe-$^{13}$C-Leu, (u) Boc-Ala-Ala-Ala-Ala-Gly-Phe-$^{13}$C-Leu, and (v) Bz-Ala-Ala-Ala-Ala-$^{13}$C-Gly-Phe-Leu.

This specification includes part or all of the contents as disclosed in the specifications and/or drawings of Japanese Patent Application Nos. 324128/1999, 149496/1999 and 157855/1998, which are priority documents of the present application.

BRIEF DESCRIPTION OF THE DRAWINGS

FIG. 5 shows the distribution of values for the chronic pancreatitis rats (○, n=10) and the normal rats (○, n=10) in the PFD and Bz-Gly-($^{13}$C-Leu) ($^{13}$C-BGL) breath tests. Each rat was subjected to the PFD test prior to the Bz-Gly-($^{13}$C-Leu) breath test. The sensitivity (the ratio of true test positives to total true positives) is shown below for each distribution drawing when a cut off value (bar) is set such that the specificity (the ratio of true test negative to total true negatives) is 100%.

DESCRIPTION OF THE INVENTION

Figure 1:
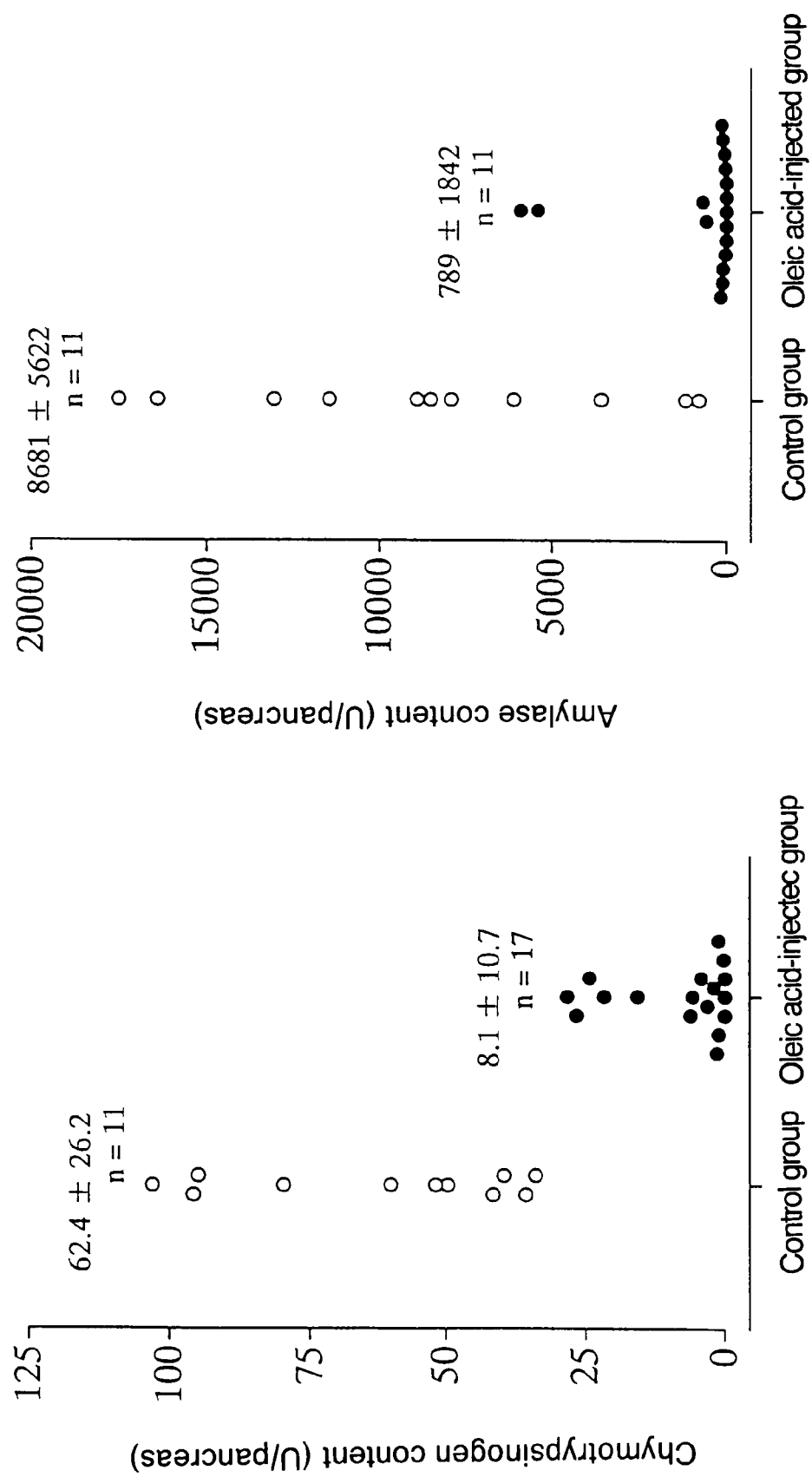
FIG. 1 shows chymotrypsinogen and amylase contents in the pancreas of an oleic acid-injected group and a control group. For the oleic acid-injected group (○), 50 μl of oleic acid was injected into the pancreatic duct of 17 Wistar male rats of 5-weeks old (n=17). For the control group (○), only laparotomy was carried out (n=11). After the treatment, the rats of both groups were kept for 3 weeks. Then, the pancreas were removed and the chymotrypsinogen and amylase contents were determined.

Hereinafter, the present invention will be described in detail.

Peptides are herein indicated in such a manner that the N-termini are on the left and the C-termini are on the right.

Amino acid residues are shown in three-letter abbreviations. Unless otherwise indicated, amino acids may be L- or D-isomers, or DL-mixtures.

The "amino acid" refers herein to any compounds having carboxyl and amino groups in the molecule and includes imino acids such as proline and hydroxyproline and compounds having a lactam structure in the molecule. The amino acids may be L- or D-isomers, or DL-mixtures.

The "peptide" refers herein to any compounds which are formed by linking at least two amino acids via a peptide bond and includes homomeric peptides consisting of amino acids, heteromeric peptides comprising a non-amino acid component(s), and their derivatives. The peptide has less than or equal to 100 amino acid residues.

The "amino acid or peptide containing at least one $^{13}$C or $^{14}$C atom" refers herein to any amino acid or peptide in which at least one carbon atom present in the amino acid, amino acid residues of the peptide, a modifying group or a protecting group thereof is replaced with a $^{13}$C or $^{14}$C atom, resulting in enriched $^{13}$C or $^{14}$C atoms in the amino acid or peptide molecules than found in nature.

The diagnostic agent for pancreatic exocrine function according to the present invention comprises an amino acid or a peptide containing at least one $^{13}$C or $^{14}$C atom, or a pharmaceutically acceptable salt thereof other than Bz-Tyr-$^{13}$C-PABA. The amino acid molecule may contain a $^{13}$C or $^{14}$C atom. Alternatively, when the amino acid or peptide has a modifying or protecting group, the modifying or protecting group may contain a $^{13}$C or $^{14}$C atom.

For example, the amino acid or peptide may be represented by the following formula (I):

$$X_1-R_1-Y_1 \qquad (I)$$

wherein $X_1$ is a hydrogen atom or a protecting group, $R_1$ is a peptide of 2 to 50 amino acids, an amino acid or a single bond, $Y_1$ is an amino acid optionally having a protecting group.

In the formula (I), $X_1$ is a hydrogen atom or a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Bases and Experiments of Peptide Synthesis", Nobuo Izumiya, Tetsuo Kato, Tohiko Aoyagi and Michinori Waki, published by Maruzen (1985); "Modification of Proteins", ed by Robert E. Feeney, John R. Whitaker, the American Chemical Society (1982); M. Bodanszky, "Principles of Peptides Synthesis", Springer-Verlag, Berlin (1984); and E. Schroder, K. Lubke, "The Peptides", Academic Press, N.Y. Vol. 1 (1965), Vol. 2 (1966). Concretely, examples thereof include benzoyl, acetyl, benzyloxycarbonyl, substituted benzyloxycarbonyl (such as p-nitrobenzyloxycarbonyl, p-methoxybenzyloxycarbonyl, etc.), t-butyloxycarbonyl, 9-fluorenylmethoxycarbonyl, p-toluenesulfonyl, phthalyl, formyl, trifluoroacetyl, triphenylmethyl, cyclohexyloxycarbonyl, o-nitrophenylsulfenyl, t-acyloxycarbonyl, isobornyloxycarbonyl, diphenylphosphinyl, diphenylphosphinothioyl, benzyl, alkyl, allylthiocarbonyl, o-nitrophenoxyacetyl, chloroacetyl, benzenesulfonyl, dibenzylphosphoryl, trialkylsilyl, allylidene, and acetoacetyl groups.

$R_1$ is a peptide of 2 to 50 amino acids, an amino acid or a single bond. The amino acid includes glycine, alanine, valine, leucine, isoleucine, serine, threonine, cystein, methionine, phenylalanine, tyrosine, tryptophan, aspartic acid, asparagine, glutamic acid, glutamine, arginine, lysine, histidine, proline, and ornithine.

$Y_1$ is an amino acid optionally having a protecting group. The protecting group includes any protecting groups which are generally used in the field of organic chemistry, for example, those described in "Textbook for Biochemical Experiments 1–Protein Chemistry IV", edited by Japan Biochemical Society, published by Tokyo Kagaku Dojin (1977); "Textbook for Experimental Chemistry 22–Organic Synthesis IV", edited by Japan Chemical Society, published by Maruzen (1992); "Bases and Experiments of Peptide Synthesis", Nobuo Izumiya, Tetsuo Kato, Tohiko Aoyagi and Michinori Waki, published by Maruzen (1985); "Modification of Proteins", ed by Robert E. Feeney, John R. Whitaker, the American Chemical Society (1982); M. Bodanszky, "Principles of Peptides Synthesis", Springer-Verlag, Berlin (1984); and E. Schroder, K. Lubke, "The Peptides", Academic Press, N.Y. Vol. 1 (1965), Vol. 2 (1966). Concretely, examples thereof include methyl ester, ethyl ester, benzyl ester, t-butyl ester and p-nitrobenzyl ester groups and N'-substituted hydrazide groups for protecting carboxyl groups; benzyloxycarbonyl, p-toluenesulfonyl and 2-chlorobenzyloxycarbonyl groups for protecting the ω-amino group in lysine and ornithine residues; nitro, methoxybenzyloxycarbonyl and p-toluenesulfonyl groups for protecting the guanidino group in arginine residue; benzyl and t-butyl groups for protecting the hydroxyl group in hydroxyl group-containing amino acid residues such as serine and tyrosine residues; benzyloxycarbonyl and benzyloxymethyl groups for protecting the imidazole group in histidine residue; benzyl and trityl groups for protecting the mercapto group in cystein residue; sulfoxide group for protecting the thioether group in methionine residue; and formyl group for protecting the indole group in tryptophan residue. The amino acid includes glycine, alanine, valine, leucine, isoleucine, serine, threonine, cystein, methionine, phenylalanine, tyrosine, tryptophan, aspartic acid, asparagine, glutamic acid, glutamine, arginine, lysine, histidine, proline, and ornithine.

The amino acids represented by $R_1$ and $Y_1$ and the peptides represented by $R_1$ may be modified in various manners. Such modification includes guanidylation, succinylation and acetylation of amino groups; modification of the guanidino group in arginine with a dicarbonyl compound; esterification of carboxyl groups; sulfenylsulfonation and alkylation of the thiol group in cystein; ethoxycarbonylation of the imidazole group in histidine; formation of sulfonium salts of methionine; acetylation of serine and threonine; nitration and iodination of tyrosine; and nitrophenylsulfonylation of tryptophan.

At least one of the amino acids in $R_1$, or at least an ester group in $Y_1$ when the amino acid in $Y_1$ is protected with the ester group, may be $^{13}C$- or $^{14}C$-labeled. Preferably, amino acid residues on which pancreatic exocrine proteases react are $^{13}C$- or $^{14}C$-labeled. The expression "$^{13}C$- or $^{14}C$-labeled" used herein means that a molecule is marked by introducing thereinto $^{13}C$ or $^{14}C$ and includes substitution of a constitutive carbon of a molecule with $^{13}C$ or $^{14}C$ or covalent bonding of a molecule to a $^{13}C$ or $^{14}C$-containing atomic group or molecule.

The present invention also encompasses a $^{13}C$- or $^{14}C$-labeled compound represented by the following formula (II):

$$X_2—R_2—Y_2—Z_1 \quad (II)$$

or a salt thereof, wherein $X_2$ is a hydrogen atom or a protecting group, $R_2$ is a peptide of 2 to 5 amino acids, an amino acid or a single bond, $Y_2$ is an amino acid, $Z_1$ is an amino acid optionally having a protecting group, and at least one of the amino acids in $R_2$, $Y_2$ and $Z_1$, or at least one of the protecting groups in $X_2$ and $Z_1$ when the protecting groups contain a carbon atom, is $^{13}C$ or $^{14}C$-labeled, provided that the following compounds are excluded.

L-Ala-L-Pro, L-Gly-L-Leu, L-Gly-L-Phe, L-Val-L-Leu, L-Leu-L-Leu, L-Tyr-L-Leu, Ac-D-Ala-D-Ala, L-Gly-L-Gly-OEt, L-Leu-L-Ala-OMe, Ac-L-Gly-L-Pro-OMe, Boc-L-Leu-L-Ala-OMe, L-Gly-L-Pro-L-Leu, L-Gly-L-Pro-L-Phe, L-Ala-L-Gly-L-Gly, L-Gly-L-Leu-L-Pro, L-Phe-L-Asp-L-Met, L-Gly-L-Leu-L-Pro, Dansyl-L-Tyr-L-Val-D-Ala, Cbz-L-Gly-L-Leu-L-Ala, L-Thr-L-Leu-L-Asn-Bzl, Z-L-Pro-L-Pro-L-Gly-OEt, L-Leu-L-Leu-L-Leu-L-Leu, L-Lys-L-Arg-L-Asp-L-Ser, Ac-L-Leu-L-Ala-L-Ala-L-Gln (NMe$_2$), Ac-L-Leu-L-Ala-L-Ala-L-Gln(NMe$_2$)-SEt, L-Tyr-L-Gly-L-Gly-L-Phe-L-Leu and L-Tyr-L-Gly-L-Gly-L-Phe-L-Met, wherein Ac is acetyl, Et is ethyl, Me is methyl, Boc is t-butyloxycarbonyl, Cbz is carbobenzyloxy, Bzl is benzoyl, Z is benzyloxycarbonyl, SEt is ethanethiol, and NMe$_2$ is dimethylamino.

In the formula (II), $X_2$ is a hydrogen atom or a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Bases and Experiments of Peptide Synthesis", Nobuo Izumiya, Tetsuo Kato, Tohiko Aoyagi and Michinori Waki, published by Maruzen (1985); "Modification of Proteins", ed by Robert E. Feeney, John R. Whitaker, the American Chemical Society (1982); M. Bodanszky, "Principles of Peptides Synthesis", Springer-Verlag, Berlin (1984); and E. Schroder, K. Lubke, "The Peptides", Academic Press, N.Y. Vol. 1 (1965), Vol. 2 (1966). Concretely, examples thereof include benzoyl, acetyl, benzyloxycarbonyl, substituted benzyloxycarbonyl (such as p-nitrobenzyloxycarbonyl, p-methoxybenzyloxycarbonyl, etc.), t-butyloxycarbonyl, 9-fluorenylmethoxycarbonyl, p-toluenesulfonyl, phthalyl, formyl, trifluoroacetyl, triphenylmethyl, cyclohexyloxycarbonyl, o-nitrophenylsulfenyl, t-acyloxycarbonyl, isobornyloxycarbonyl, diphenylphosphinyl, diphenylphosphinothioyl, benzyl, alkyl, allylthiocarbonyl, o-nitrophenoxyacetyl, chloroacetyl, benzenesulfonyl, dibenzylphosphoryl, trialkylsilyl, allylidene, and acetoacetyl groups.

$R_2$ is a peptide of 2 to 5 amino acids, an amino acid or a single bond. The amino acid includes glycine, alanine, valine, leucine, isoleucine, serine, threonine, cystein, methionine, phenylalanine, tyrosine, tryptophan, aspartic acid, asparagine, glutamic acid, glutamine, arginine, lysine, histidine, proline, and ornithine.

$Y_2$ is an amino acid and the amino acid includes glycine, alanine, valine, leucine, isoleucine, serine, threonine, cystein, methionine, phenylalanine, tyrosine, tryptophan, aspartic acid, asparagine, glutamic acid, glutamine, arginine, lysine, histidine, proline, and ornithine.

$Z_1$ is an amino acid optionally having a protecting group. The protecting group includes any protecting groups which are generally used in the field of organic chemistry, for example, those described in "Textbook for Biochemical Experiments 1—Protein Chemistry IV", edited by Japan Biochemical Society, published by Tokyo Kagaku Dojin (1977); "Textbook for Experimental Chemistry 22—Organic Synthesis IV", edited by Japan Chemical Society, published by Maruzen (1992); "Bases and Experiments of Peptide Synthesis", Nobuo Izumiya, Tetsuo Kato, Tohiko Aoyagi and Michinori Waki, published by Maruzen (1985); "Modification of Proteins", ed by Robert E. Feeney, John R. Whitaker, the American Chemical Society (1982); M. Bodanszky, "Principles of Peptides Synthesis", Springer-Verlag, Berlin (1984); and E. Schroder, K. Lubke, "The Peptides", Academic Press, N.Y. Vol. 1 (1965), Vol. 2 (1966). Concretely, examples thereof include methyl ester, ethyl ester, benzyl ester, t-butyl ester and p-nitrobenzyl ester groups and N'-substituted hydrazide groups for protecting carboxyl groups; benzyloxycarbonyl, p-toluenesulfonyl and 2-chlorobenzyloxycarbonyl groups for protecting the ω-amino group in lysine and ornithine residues; nitro, methoxybenzyloxycarbonyl and p-toluenesulfonyl groups for protecting the guanidino group in arginine residue; benzyl and t-butyl groups for protecting the hydroxyl group in hydroxyl group-containing amino acid residues such as serine and tyrosine residues; benzyloxycarbonyl and benzyloxymethyl groups for protecting the imidazole group in histidine residue; benzyl and trityl groups for protecting the mercapto group in cystein residue; sulfoxide group for protecting the thioether group in methionine residue; and formyl group for protecting the indole group in tryptophan residue. The amino acid includes glycine, alanine, valine, leucine, isoleucine, serine, threonine, cystein, methionine, phenylalanine, tyrosine, tryptophan, aspartic acid, asparagine, glutamic acid, glutamine, arginine, lysine, histidine, proline, and ornithine.

The amino acids represented by $R_2$, $Y_2$ and $Z_1$ and the peptides represented by $R_2$ may be modified in various manners. Such modification includes guanidylation, succinylation and acetylation of amino groups; modification of the guanidino group in arginine with a dicarbonyl compound; esterification of carboxyl groups; sulfenylsulfonation and alkylation of the thiol group in cystein; ethoxycarbonylation of the imidazole group in histidine; formation of sulfonium salts of methionine; acetylation of serine and threonine; nitration and iodination of tyrosine; and nitrophenylsulfonylation of tryptophan.

At least one of the amino acids in $R_2$, $Y_2$ and $Z_1$, or at least one of the protecting groups in $X_2$ and $Z_1$ when the protecting groups contain a carbon atom, is $^{13}C$ or $^{14}C$-labeled.

Preferably, $Z_1$ is a $^{13}C$- or $^{14}C$-labeled amino acid optionally having a protecting group.

In one embodiment of the present invention, the $^{13}C$- or $^{14}C$-labeled compound, or salt thereof may be as follows:

1) in the case where $X_2$ is a protecting group and $R_2$ is a single bond,
　1-i) when $Z_1$ is D-Ala, $Y_2$ is an amino acid other than D-Ala,
　1-ii) when $Z_1$ is L-Ala-OMe, $Y_2$ is an amino acid other than L-Leu,
　1-iii) when $Z_1$ is L-Pro-OMe, $Y_2$ is an amino acid other than L-Gly, 2) in the case where $X_2$ is a protecting group and $R_2$ is an amino acid,
　2-i) when $Z_1$ is D-Ala, $Y_2$ is an amino acid other than L-Val,
　2-i) when $Z_1$ is L-Ala, $Y_2$ is an amino acid other than L-Leu,
　2-iii) when $Z_1$ is L-Gly-OEt, $Y_2$ is an amino acid other than L-Pro, 3) in the case where $X_2$ is a protecting group, $R_2$ is a peptide of 2 amino acids and $Z_1$ is L-Gln optionally having SEt, $Y_2$ is an amino acid other than L-Ala, 4) in the case where $X_2$ is a hydrogen atom and $R_2$ is a single bond,
　4-i) when $Z_1$ is L-Pro, $Y_2$ is an amino acid other than L-Ala,
　4-ii) when $Z_1$ is L-Leu, $Y_2$ is an amino acid other than L-Gly, L-Val, L-Leu and L-Tyr,
　4-iii) when $Z_1$ is L-Phe, $Y_2$ is an amino acid other than L-Gly,
　4-iv) when $Z_1$ is L-Gly-OEt, $Y_2$ is an amino acid other than L-Gly,
　4-v) when $Z_1$ is L-Ala-OMe, $Y_2$ is an amino acid other than L-Leu, 5) in the case where $X_2$ is a hydrogen atom and $R_2$ is an amino acid,
　5-i) when $Z_1$ is L-Leu, $Y_2$ is an amino acid other than L-Pro,
　5-ii) when $Z_1$ is L-Phe, $Y_2$ is an amino acid other than L-Pro,
　5-iii) when $Z_1$ is L-Gly, $Y_2$ is an amino acid other than L-Gly,
　5-iv) when $Z_1$ is L-Pro, $Y_2$ is an amino acid other than L-Leu,
　5-v) when $Z_1$ is L-Met, $Y_2$ is an amino acid other than L-Asp,
　5-vi) when $Z_1$ is L-Asn-Bzl, $Y_2$ is an amino acid other than L-Leu, 6) in the case where $X_2$ is a hydrogen atom and $R_2$ is a peptide of 2 amino acids,
　6-i) when $Z_1$ is L-Leu, $Y_2$ is an amino acid other than L-Leu,
　6-i) when $Z_1$ is L-Ser, $Y_2$ is an amino acid other than L-Asp, and 7) in the case where $X_2$ is a hydrogen atom and $R_2$ is a peptide of 3 amino acids,
　7-i) when $Z_1$ is L-Leu, $Y_2$ is an amino acid other than L-Phe,
　7-ii) when $Z_1$ is L-Met, $Y_2$ is an amino acid other than L-Phe.

In another embodiment of the present invention, the $^{13}$C- or $^{14}$C-labeled compound, or salt thereof may be as follows:

1) in the case where $X_2$ is a protecting group selected from the group consisting of Dansyl, Cbz, Ac and Z, and $R_2$ is an amino acid or a peptide of 2 amino acids, 1-i) when $Z_1$ is D-Ala, $Y_2$ is an amino acid other than L-Val, 1-ii) when $Z_1$ is L-Ala, $Y_2$ is an amino acid other than L-Leu, 1-iii) when $Z_1$ is L-Gly-OEt, $Y_2$ is an amino acid other than L-Pro, 1-iv) when $Z_1$ is L-Gln(NMe$_2$) or L-Gln(NMe$_2$)-SEt, $Y_2$ is an amino acid other than L-Ala, 2) in the case where $X_2$ is Ac or Boc, and $R_2$ is a single bond, 2-i) when $Z_1$ is D-Ala, $Y_2$ is an amino acid other than D-Ala, 2-ii) when $Z_1$ is L-Pro-OMe, $Y_2$ is an amino acid other than L-Gly, 2-iii) when $Z_1$ is L-Ala-OMe, $Y_2$ is an amino acid other than L-Leu, 3) in the case where $X_2$ is a hydrogen atom and $R_2$ is an amino acid or a peptide of 2 or 3 amino acids, 3-i) when $Z_1$ is L-Leu, $Y_2$ is an amino acid other than L-Pro, L-Leu and L-Phe, 3-ii) when $Z_1$ is L-Phe, $Y_2$ is an amino acid other than L-Pro, 3-iii) when $Z_1$ is L-Gly, $Y_2$ is an amino acid other than L-Gly, 3-iv) when $Z_1$ is L-Pro, $Y_2$ is an amino acid other than L-Leu, 3-v) when $Z_1$ is L-Met, $Y_2$ is an amino acid other than L-Asp and L-Phe, 3-vi) when $Z_1$ is L-Asn-Bzl, $Y_2$ is an amino acid other than L-Leu, 3-vii) when $Z_1$ is L-Ser, $Y_2$ is an amino acid other than L-Asp, and 4) in the case where $X_2$ is a hydrogen atom and $R_2$ is a single bond, 4-i) when $Z_1$ is L-Pro, $Y_2$ is an amino acid other than L-Ala, 4-ii) when $Z_1$ is L-Leu, $Y_2$ is an amino acid other than L-Gly, L-Val, L-Leu and L-Tyr, 4-iii) when $Z_1$ is L-Phe, $Y_2$ is an amino acid other than L-Gly, 4-iv) when $Z_1$ is L-Gly-OEt, $Y_2$ is an amino acid other than L-Gly, 4-v) when $Z_1$ is L-Ala-OMe, $Y_2$ is an amino acid other than L-Leu.

In formula (II), it is preferred that $X_2$ is selected from the group consisting of Ac, Bz (benzoyl), Boc, Z and a hydrogen atom.

Also, in formula (II), it is preferred that $X_2$ is a protecting group and $R_2$ is a single bond.

In a preferred embodiment of the present invention, (1) at least one of the amino acids in $Y_2$ and $Z_1$ is Arg or Lys (this is a suitable substrate for trypsin), (2) at least one of the amino acids in $Y_2$ and $Z_1$ is an aromatic amino acid, Leu, His or Met (this is a suitable substrate for chymotrypsin), (3) at least one of the amino acids in $Y_2$ and $Z_1$ is a neutral and non-aromatic amino acid (this is a suitable substrate for elastase), (4) the amino acid in $Z_1$ is an amino acid other than Arg, Lys and Pro (this is a suitable substrate for carboxypeptidase A), or (5) the amino acid in $Z_1$ is Arg or Lys (this is a suitable substrate for carboxypeptidase B).

In a more preferred embodiment of the present invention, $X_2$ is selected from the group consisting of a hydrogen atom, Bz, Ac and Boc, $Y_2$ is selected from the group consisting of Phe, Ala, Gly, Tyr and Arg, $Z_1$ is selected from the group consisting of Leu optionally having a protecting group, Ala optionally having a protecting group, and Gly optionally having a protecting group, for example, the group consisting of Leu, Ala, Gly, Leu-OMe, Leu-OEt, Ala-OMe, Ala-OEt, Gly-OMe and Gly-OEt, and more specifically, the group consisting of $^{13}$C- or $^{14}$C-Leu, $^{13}$C- or $^{14}$C-Ala, $^{13}$C- or $^{14}$C-Gly, $^{13}$C- or $^{14}$C-Leu-OMe, $^{13}$C- or $^{14}$C-Leu-OEt, $^{13}$C- or $^{14}$C-Ala-OMe, $^{13}$C- or $^{14}$C-Ala-OEt, $^{13}$C- or $^{14}$C-Gly-OMe and $^{13}$C- or $^{14}$C-Gly-OEt.

In a still more preferred embodiment of the present invention, the $^{13}$C- or $^{14}$C-labeled compound represented by formula (II), or salt thereof is selected from the group consisting of the following compounds:

(a) Phe-$^{13}$C-Leu, (b) Arg-$^{13}$C-Leu (c) Bz-Ala-$^3$C-Ala, (d) Bz-Gly-$^3$C-Leu, (e) Bz-Phe-$^{13}$C-Gly, (f) Bz-Tyr-$^{13}$C-Leu (g) Bz-Phe-$^3$C-Leu, (h) Bz-(DL)Phe-$^{13}$C-Leu, (j) Bz-Arg-$^{13}$C-Leu, (k) Ac-Phe-$^{13}$C-Leu, (l) Ac-Tyr-$^{13}$C-Leu, (m) Bz-Ala-$^{13}$C-Ala-OMe, (n) Bz-Gly-$^{13}$C-Leu-OMe, (o) Bz-Phe-$^{13}$C-Gly-OMe, (p) Bz-Phe-$^{13}$C-Leu-OMe, (q) Bz-(DL)Phe-$^{13}$C-Leu-OMe, (r) Ac-Phe-$^{13}$C-Leu-OMe, (s) Ac-Tyr-$^{13}$C-Leu-OMe, (t) Bz-Ala-Ala-Ala-Ala-Gly-Phe-$^{13}$C-Leu, (u) Boc-Ala-Ala-Ala-Ala-Gly-Phe-$^{13}$C-Leu, and (v) Bz-Ala-Ala-Ala-Ala-$^{13}$C-Gly-Phe-Leu The $^{13}$C- or $^{14}$C-labeled compounds represented by the above formula (I) and pharmaceutically acceptable salts thereof and the $^{13}$C- or $^{14}$C-labeled compounds represented by the above formula (II) and salts thereof may be absorbed through the digestive tract after the reaction of a protease or proteases, and decarboxylated by metabolic action to generate $^{13}CO_2$ or $^{14}CO_2$. The protease or proteases may be pancreatic exocrine proteases including chymotrypsin, trypsin, elastase, and carboxypeptidases represented by carboxypeptidase A and B.

Chymotrypsin specifically cleaves the carboxyl terminal peptide linkage of tyrosine, tryptophan, phenylalanine, leucine, histidine or methionine residue and also acts on esters and amides containing these residues.

Trypsin catalyzes the hydrolysis of peptide linkages at the carboxyl terminus of an arginine residue, a lysine residue, and an S-aminoethylcysteine residue produced by artificial reactions. Further, chemical synthetic products containing an (allyl)amide or ester linkage instead of the peptide linkage may be substrates for trypsin so long as they are derived from the three amino acids.

Elastase hydrolyzes the peptide linkage at the carboxyl terminus of alanine, glycine, valine, leucine, isoleucine and methionine residues, which are uncharged non-aromatic amino acids. It is known that succinyl-(alanyl)3-p-nitroanilide may be an artificial substrate therefor.

Carboxypeptidase B has an action to sequentially cleave from the carboxyl terminus basic amino acids such as arginine and lysine.

Carboxypeptidase A has an action to sequentially cleave from the carboxyl terminus aromatic hydrophobic amino acids such as tyrosine, phenylalanine, tryptophan, leucine, isoleucine, threonine, glutamine, histidine, alanine, valine, asparagine, serine, lysine, glycine, aspartic acid and glutamic acid.

By taking into consideration such substrate specificities of proteases as above described, $^{13}$C- or $^{14}$C-labeled compounds or salts thereof suitable for use in diagnostic agents for pancreatic exocrine function may be designed.

The $^{13}$C- or $^{14}$C-labeled compounds may be synthesized in a known manner using commercially available amino acids. For example, methods described in "Textbook for Experimental Chemistry 22—Organic Synthesis IV", edited by Japan Chemical Society, published by Maruzen (1992) may be used. One illustrative example thereof will be described below.

A $^{13}$C-labeled amino acid is dissolved in hydrogen chloride/methanol and refluxed. The resulting methyl ester is suspended in dichloromethane and triethylamine is then dropwise added while being ice-cooled and stirred. Further, an N-benzoyl-amino acid, 1-hydroxy-1H-benzotriazole.H$_2$O(HOBt) and dichloromethane are added. Then, a solution of 1-ethyl-3-(3-dimethylaminopropyl)-carbodiimide.HCl (WSC) dissolved in dichloromethane is added and the mixture is stirred. After concentration, the reaction mixture is extracted with ethyl acetate, washed with 1N HCl, 5% NaHCO$_3$, and water, dried over magnesium sulfate, and evaporated to dryness, or further saponified, to yield the desired $^{13}$C-labeled compound represented by the formula (I).

The $^{13}$C- or $^{14}$C-labeled compounds may be obtained in the form of a salt. The salts may include those with inorganic acids such as hydrochloric, sulfuric, nitric and phosphoric acids; with organic acids such as formic, acetic, propionic, glycolic, succinic, malic, tartaric, citric and trifluoroacetic acids; with alkali metals such as sodium and potassium; with alkaline earth metals such as calcium; and with organic amines such as ammonium, ethanolamine, triethylamine and dicyclohexylamine.

The test using the agents for pancreatic exocrine function according to the present invention may be carried out by administering to a subject an amino acid or a peptide containing at least one $^{13}$C or $^{14}$C atom or pharmaceutically acceptable salt thereof. A test is possible in which the concentration of the $^{13}$C- or $^{14}$C-labeled compound is measured in serum, urine or stool after the administration, however, a breath test is desirable in which an increase in $^{13}$C or $^{14}$C concentration is measured in the exhaled CO$_2$ after the administration. When the amino acid or a peptide containing at least one $^{13}$C or $^{14}$C atom or pharmaceutically acceptable salt thereof is administered to a subject, a test meal or the like may be ingested by the subject to induce secretion of pancreatic enzymes. Also, two or more amino acids or peptides containing at least one $^{13}$C or $^{14}$C atom or pharmaceutically acceptable salts thereof may be combined for use. Concretely, in the cases of $^{13}$C, the $^{13}$C concentration is determined in the exhaled CO$_2$ after the administration, then the pancreatic exocrine function is diagnosed from either the data of the degree of increase ($\Delta^{13}$C(‰)) of the $^{13}$C concentration in the exhaled CO$_2$ at predetermined times (e.g., 5, 10 and 15 minutes) after the administration, or the data associated with the time course (onset slope, change in slope, peak time, etc.) in the degree of increase ($\Delta^{13}$C(‰)) of the $^{13}$C concentration in the exhaled CO$_2$ during a predetermined period after the administration. In the cases of $^{14}$C, the $^{14}$C concentration, i.e., radioactivity, is determined in the exhaled CO$_2$ after the administration; and the pancreatic exocrine function is diagnosed from either the data of the quantity of radioactivity in the exhaled CO$_2$ at predetermined times (e.g., 5, 10 and 15 minutes) after the administration, or the data associated with the time course (onset slope, change in slope, peak time, etc.) in the rate increase of radioactivity in the exhaled CO$_2$ during a predetermined period after the administration. These test methods utilize the phenomenon that when the amino acid or a peptide containing at least one $^{13}$C or $^{14}$C atom is administered to a subject, the compound is absorbed through the digestive tract after the reaction of a protease or proteases, and decarboxylated by metabolic action in the body to generate $^{13}$CO$_2$ or $^{14}$CO$_2$.

The $^{13}$C concentration in the exhaled CO$_2$ can be determined by gas chromatography-mass spectrometry (GC-MS), infrared spectroscopy, mass spectrometry, photoelectric acoustic spectroscopy, NMR (nuclear magnetic resonance), and other methods.

The $^{14}$C concentration or radioactivity in the exhaled CO$_2$ may be measured from the breath of a subject, directly or after trapping CO$_2$ in a solvent, with a GM counter, a liquid scintillation counter, a solid scintillation counter, autoradiography, an ionization chamber, or the like.

The diagnostic agent for pancreatic exocrine function according to the present invention may be formulated from the $^{13}$C- or $^{14}$C-labeled compound represented by the formula (I) or pharmaceutically acceptable salt thereof alone or in combination with an excipient or carrier into an oral preparation such as a tablet, capsule, powder, granule, liquid, etc. The excipient or carrier may be any pharmaceutically acceptable one ordinarily used in this field and its nature and composition may be appropriately chosen. For example, water may be used as a liquid carrier. Solid carriers include cellulose derivatives such as hydroxypropyl cellulose, and organic acid salts such as magnesium stearate. Also, freeze-dried preparations may be used.

The $^{13}$C- or $^{14}$C-labeled compound represented by the formula (I) or pharmaceutically acceptable salt thereof is contained in the agent in variable amounts depending on the nature of the agent, but generally in an amount of 1 to 100% by weight, preferably 50 to 100% by weight. In a capsule, tablet, granule or powder preparation, the $^{13}$C- or $^{14}$C-labeled compound represented by the formula (I) or pharmaceutically acceptable salt thereof is contained in the preparation in an amount of about 10 to 100% by weight, preferably 50 to 100% by weight, the balance being a carrier.

The dose of the diagnostic agent for pancreatic exocrine function according to the present invention should be sufficient to determine or confirm an increase of $^{13}$CO$_2$ or

EXAMPLES

Hereinbelow, the present invention is illustrated in more detail by the following examples, however the scope of the present invention shall not be limited by the example. In the following examples, amino acids shown in three-letter abbreviations are L-isomers unless otherwise indicated.

Example 1

Preparation of Bz-DL-Phe-($^{13}$C-Leu)-OMe

After 1 g of 1-$^{13}$C-L-leucine (Masstrace) was dissolved in hydrogen chloride/methanol and refluxed, the resulting $^{13}$C-L-leucine methyl ester was suspended in 50 ml of dichloromethane and 1.08 ml of triethylamine was added dropwise under while being ice-cooled and stirred. Further, 2.0 g of N-benzoyl-DL-phenylalanine, 2.34 g of HOBt (1-hydroxy-1H-benzotriazole.H$_2$O) and 50 ml of dichloromethane were added. Then, a solution of 1.49 g of WSC (1-ethyl-3-(3-dimethylaminopropyl)-carbodiimide.HCl) dissolved in 100 ml of dichloromethane was added and stirred for 1 hour under while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 2.32 g of Bz-DL-Phe-($^{13}$C-Leu)-OMe.

Example 2

Preparation of Bz-DL-Phe-($^{13}$C-Leu) and its Sodium Salt (Bz-DL-Phe-($^{13}$C-Leu).Na)

After 2.32 g of Bz-DL-Phe-($^{13}$C-Leu)-OMe was dissolved in 100 ml of methanol, 6.4 ml of 1N NaOH was added dropwise under while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 1.93 g of Bz-DL-Phe-($^{13}$C-Leu), which was then recrystallized with ethyl acetate.

The structure and $^{13}$C-labeled position were confirmed by $^{13}$C-NMR and mass spectrometry.

$^{13}$C-NMR (methanol-d4, 300 MHz): 175.8 ppm ($^{13}$COOH)

Mass spectrometry (m/z): 383 (M$^+$), 365, 224, 131, 105, 77

LC-MS (m/z): 384 (M$^+$+H), 252, 224, 105

The sodium salt of Bz-DL-Phe-($^{13}$C-Leu) was obtained by neutralizing Bz-DL-Phe-($^{13}$C-Leu) with an equivalent of 1M sodium carbonate followed by lyophilization.

Example 3

Degradation of Bz-DL-Phe-($^{13}$C-Leu) by Chymotrypsin

Bz-DL-Phe-($^{13}$C-Leu) was reacted with chymotrypsin and the degradation product, leucine, generated upon action of chymotrypsin was quantitatively determined by ninhydrin reaction. The reaction was carried out in 20 mM HEPPS-Na (pH 8.0), 23 mM Bz-DL-Phe-($^{13}$C-Leu), 0.16 mg/ml chymotrypsin (from bovine pancreas, Worthington Biochemical Corporation, #1432, Lot 37A906) at 37° C. for 15 minutes. After reaction, 50 μl of citrate buffer (citric acid monohydrate), 20 μl of ninhydrin solution (50 mg/ml solution in methyl cellosolve) and 100 μl of KCN solution (0.01 M aqueous KCN solution diluted 50 times with methyl cellosolve) were added to 100 μl of the reaction mixture and heated at 100° C. for 15 minutes. After cooling the ninhydrin reaction mixture to room temperature, 150 μl of 60% (V/V) ethanol was added to 100 μl of the ninhydrin reaction mixture and stirred followed by determination of an absorbance at a wave length of 570 nm. An experiment wherein all the reactions that were carried out without adding Bz-DL-Phe-($^{13}$C-Leu) was taken as a "blank," and leucine was used as a standard.

Bz-DL-Phe-($^{13}$C-Leu) was degraded upon reaction with chymotrypsin to produce leucine. The rate of degradation was 1.72 nmole/mg chymotrypsin/min. From these results, it was confirmed that Bz-DL-Phe-($^{13}$C-Leu) could be a substrate for chymotrypsin.

Example 4

Preparation of Bz-Ala-($^{13}$C-Ala)-OMe

After 2 g of 1-$^{13}$C-L-alanine (Masstrace) was dissolved in hydrogen chloride/methanol and refluxed, the resulting $^{13}$C-L-alanine methyl ester was suspended in 100 ml of dichloromethane and 4.0 ml of triethylamine was added dropwise while being ice-cooled and stirred. Further, 5.6 g of N-benzoyl-L-alanine, 8.9 g of HOBt and 100 ml of dichloromethane were added. Then, a solution of 5.6 g of WSC dissolved in 200 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 4.38 g of Bz-Ala-($^{13}$C-Ala)-OMe.

Example 5

Preparation of Bz-Ala-($^{13}$C-Ala) and its Sodium Salt

After 4.38 g of Bz-Ala-($^{13}$C-Ala)-OMe was dissolved in 100 ml of methanol, 16 ml of 1N NaOH was added dropwise while being ice-cooled and stirred followed by heating and stirring at 70° C. for 2 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 2.85 g of Bz-Ala-($^{13}$C-Ala), which was then recrystallized with ethyl acetate.

The structure and $^{13}$C-labeled position were confirmed by $^{13}$C-NMR and mass spectrometry.

$^{13}$C-NMR (methanol-d4, 300 MHz): 175.9 ppm ($^{13}$COOH)

LC-MS (m/z): 266 (M$^+$+H), 176, 148, 105

The sodium salt of Bz-Ala-($^{13}$C-Ala) was obtained by neutralizing Bz-Ala-($^{13}$C-Ala) with an equivalent of 1M sodium carbonate followed by lyophilization.

Example 6

Preparation of Bz-Gly-($^{13}$C-Leu)-OMe

After 2 g of 1-$^{13}$C-L-leucine (Masstrace) was dissolved in hydrogen chloride/methanol and refluxed, the resulting $^{13}$C-L-leucine methyl ester was suspended in 100 ml of dichloromethane and 2.4 ml of triethylamine was added dropwise while being ice-cooled and stirred. Further, 3.0 g of N-benzoylglycine, 5.1 g of HOBt and 100 ml of dichloromethane were added. Then, a solution of 3.3 g of WSC dissolved in 200 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 4.38 g of Bz-Gly-($^{13}$C-Leu)-OMe.

Example 7

Preparation of Bz-Gly-($^{13}$C-Leu) and its Sodium Salt

After 4.38 g of Bz-Gly-($^{13}$C-Leu)-OMe was dissolved in 100 ml of methanol, 15 ml of 1N NaOH was added dropwise while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 3.83 g of Bz-Gly-($^{13}$C-Leu), which was then recrystallized with ethyl acetate.

The structure and $^{13}$C-labeled position were confirmed by $^{13}$C-NMR and mass spectrometry.

$^{13}$C-NMR (CDCl$_3$, 300 MHz): 175.5 ppm ($^{13}$COOH)

Mass spectrometry (m/z): 293 (M$^+$), 275, 134, 105, 77

LC-MS (m/z): 294 (M$^+$+H), 162, 134, 105

The sodium salt of Bz-Gly-($^{13}$C-Leu) was obtained by neutralizing Bz-Gly-($^{13}$C-Leu) with an equivalent of 1M sodium carbonate followed by lyophilization.

Example 8

Preparation of Bz-DL-Phe-($^{13}$C-Gly)-OMe

After 570 mg of 1-$^{13}$C-glycine (Masstrace) was dissolved in hydrogen chloride/methanol and refluxed, the resulting $^{13}$C-glycine methyl ester was suspended in 50 ml of dichloromethane and 1 ml of triethylamine was added dropwise while being ice-cooled and stirred. Further, 2.0 g of N-benzoyl-DL-phenylalanine, 2.3 g of HOBt and 50 ml of dichloromethane were added. Then, a solution of 1.41 g of WSC dissolved in 100 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 2.11 g of Bz-DL-Phe-($^{13}$C-Gly)-OMe.

Example 9

Preparation of Bz-DL-Phe-($^{13}$C-Gly) and its Sodium Salt

After 2.11 g of Bz-DL-Phe-($^{13}$C-Gly)-OMe was dissolved in 100 ml of methanol, 6.9 ml of 1N NaOH was added dropwise while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 1.3 g of Bz-DL-Phe-($^{13}$C-Gly).

The structure and $^{13}$C-labeled position were confirmed by $^{13}$C-NMR and mass spectrometry.

$^{13}$C-NMR (CDCl$_3$, 300 MHz): 179.2 ppm ($^{13}$COOH)

Mass spectrometry (m/z): 327 (M$^+$), 309, 224, 161, 105, 77

LC-MS (m/z): 328 (M$^+$+H), 252, 224, 105

The sodium salt of Bz-DL-Phe-($^{13}$C-Gly) was obtained by neutralizing Bz-DL-Phe-($^{13}$C-Gly) with an equivalent of 1M sodium carbonate followed by lyophilization.

Example 10

Preparation of Ac-Phe-($^{13}$C-Leu)-OMe

After 1.16 g of 1$^{13}$C-L-leucine (Masstrace) was dissolved in hydrogen chloride/methanol and refluxed, the resulting $^{13}$C-L-leucine methyl ester was suspended in 50 ml of dichloromethane and 1.2 ml of triethylamine was added dropwise while being ice-cooled and stirred. Further, 1.8 g of N-acetyl-L-phenylalanine, 2.7 g of HOBt and 50 ml of dichloromethane were added. Then, a solution of 1.7 g of WSC dissolved in 100 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 2.62 g of Ac-Phe-($^{13}$C-Leu)-OMe.

Example 11

Preparation of Ac-Phe-($^{13}$C-Leu) and its Sodium Salt

After 2.62 g of Ac-Phe-($^{13}$C-Leu)-OMe was dissolved in 100 ml of methanol, 9.3 ml of 1N NaOH was added dropwise while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 2.44 g of Ac-Phe-($^{13}$C-Leu), which was then recrystallized with ethyl acetate.

The structure and $^{13}$C-labeled position were confirmed by $^{13}$C-NMR and mass spectrometry.

$^{13}$C-NMR (CDCl$_3$, 300 MHz): 175.9 ppm ($^{13}$COOH)

LC-MS (m/z): 322 (M$^+$+H), 190, 162, 120

The sodium salt of Ac-Phe-($^{13}$C-Leu) was obtained by neutralizing Ac-Phe-($^{13}$C-Leu) with an equivalent of 1M sodium carbonate followed by lyophilization.

Example 12

Preparation of Ac-Tyr-($^{13}$C-Leu)-OMe

After 0.98 g of 1-$^{13}$C-L-leucine (Masstrace) was dissolved in hydrogen chloride/methanol and refluxed, the resulting $^{13}$C-L-leucine methyl ester was suspended in 50 ml of dichloromethane and 1.0 ml of triethylamine was added dropwise while being ice-cooled and stirred. Further, 1.65 g of N-acetyl-L-tyrosine, 2.26 g of HOBt and 50 ml of dichloromethane were added. Then, a solution of 1.42 g of WSC dissolved in 100 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% NaHCO$_3$, and water, dried over magnesium sulfate, and concentrated to dryness to yield 2.14 g of Ac-Tyr-($^{13}$C-Leu)-OMe.

Example 13

Preparation of Ac-Tyr-($^{13}$C-Leu) and its Sodium Salt

After 2.14 g of Ac-Tyr-($^{13}$C-Leu)-OMe was dissolved in 100 ml of methanol, 7.3 ml of 1N NaOH was added dropwise while being ice-cooled and stirred followed by heating and stirring at 70° C. for 2.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% NaHCO$_3$. After washing with ethyl acetate, 5% NaHCO$_3$ was acidified with 1N—HCl. The reaction mixture was extracted with ethyl acetate, washed with water, dried over magnesium sulfate, and concentrated to dryness to yield 1.36 g of Ac-Tyr-($^{13}$C-Leu), which was then recrystallized with ethyl acetate.

The structure and $^{13}$C-labeled position were confirmed by $^{13}$C-NMR and mass spectrometry.

$^{13}$C-NMR (methanol-d4, 300 MHz): 175.8 ppm ($^{13}$COOH)

LC-MS (m/z): 338 (M$^+$+H), 206, 178, 136

The sodium salt of Ac-Tyr-($^{13}$C-Leu) was obtained by neutralizing Ac-Tyr-($^{13}$C-Leu) with an equivalent of 1M sodium carbonate followed by lyophilization.

Example 14

Preparation of a Model of Chronic Pancreatitis in Rats 14-1 Method for preparation A model of chronic pancreatitis in rats were prepared by injecting oleic acid into the pancreatic duct (Mundlos et al., Pancreas 1:29 (1986)). After overnight fast, a Wistar male rat of 5 weeks old was anesthetized by intraperitoneal administration of Nembutal (50 mg/kg). The abdominal wall was shaved and the rat was fixed supinely on an operating table. An Isodine solution was applied to sterilize, and a 3 to 4 cm midline incision was made on the abdomen. The duodenum and the pancreas were drawn out and a 25 G needle was pierced through the duodenal wall. A polyethylene cannula (PE-10) was inserted through the pierced hole into the duodenum and further inserted into the common bile duct by about 5 mm from the papilla. The inserted cannula was fixed by a microclip. Further, the biliary duct was closed by a microclip in order to prevent oleic acid from flowing into the liver. Oleic acid (50 μl) was injected at a rate of 20 μl/min by a microsyringe pump. After the injection was completed, the rat was allowed to stand for 2 minutes so that the oleic acid was distributed throughout the pancreas. The microclips and cannula were removed and the duodenum was returned. The endothelium was sutured with silk thread (Nescosuture silk suture thread 3-0, Nihon Shoji KK) and the outer skin was sutured with a skin stapler (Appose ULC, No. 8034-12, 5.7×3.8 mm). As a control, only laparotomy was carried out. These rats subjected to the operation were kept under free intake of standard food and water at 23° C., relative humidity of 55% until use.

14-2 Evaluation

After injecting oleic acid into the pancreatic duct and being kept for 3 weeks, these rats (oleic acid-injected rats) were subjected to measurement of amylase in the blood, and to quantitative determination of chymotrypsinogen and amylase contents in the pancreas (FIG. 1). An extraction buffer (20 mM HEPPS+Na, pH 8.0, 100 mM KCl, 0.5% (w/v) Triton X-100) was added to the removed pancreas to the total volume of 10 ml. The material was subjected to ultrasonic disruption (Bionic 7250, Seiko, Sonics & Materials) and centrifuged at 10,000×g for 20 minutes to yield a pancreatic extract as a supernatant. To 200 μl of the pancreatic extract, 200 μl of 1 mg/ml trypsin (from porcine pancreas, Biozyme, code TRY1, batch 0196), which was 5 mg/ml trypsin, 1 mM acetate buffer, pH 3.2, five times diluted with 20 mM Hepes-Na, pH 8.0, was added and allowed to stand at 4° C. for 2 hours to activate chymotrypsinogen to chymotrypsin (Lampel and Kern, Virchows Archiv A 373:97 (1977)). After adding 30 μl of the activated pancreatic extract and 20 μl of 123.8 mM BT-PABA to 150

μl of 20 mM HEPPS-Na, pH 8.0, the chymotrypsin reaction was performed at 37° C. for 15 minutes. After the reaction, 10 μl of 100% (W/V) TCA solution was added and centrifuged at 15,000×g for 5 minutes and the PABA in the supernatant was quantitatively determined using a PABA measuring kit (Eisai). The amylase activity in the pancreatic extract was measured using Fuji Dri-Chem. Both units of activity (U) show μ mole release/min.

The chymotrypsinogen content was 62.4 U±26.2, n=11 in the control rats and 8.1 U±10.7, n=17 in the oleic acid-injected rats. The amylase content was 8681 U±5622, n=11 in the control rats and 789 U±1842, n=17 in the oleic acid-injected rats. Thus, Both enzyme contents were significantly reduced in the oleic acid-injected rats (FIG. 1). In particular, the chymotrypsinogen content was markedly reduced. Therefore, pancreatitis can be evaluated to have occurred in 12 rats among 17 oleic acid-injected rats (70%), if the normal lower limit is the mean−2SD of chymotrypsinogen content for the control. On the other hand, the blood amylase concentrations of both rats were at the same level, which increases in the acute period of pancreatitis, 1930 U±823, n=11 in the control rats and 2137 U±668, n=17 in the oleic acid-injected rats; therefore, the oleic acid-injected rats are characterized as a model of chronic pancreatitis.

Example 15

Bz-DL-Phe-($^{13}$C-Leu) Breath Test 15-1 Method

The rats of the model of chronic pancreatitis and control rats, which were kept for 3 to 4 weeks after the operation, were made to fast from 9:00 AM. At 4:00 PM, 3 mg/ml of BT-PABA (PFD solution for internal use, Eisai) was orally administered in an amount of 15 mg/kg. Urine was collected for 16 hours until 9:00 AM of the next day. The amount of the collected urine and the PABA concentration in the urine were determined using a PABA measuring kit to determine the excretion rate in urine (PFD test).

After the PFD test, Bz-DL-Phe-($^{13}$C-Leu).Na dissolved in distilled water (250 mg/kg, 6 ml/kg) was orally administered to the rats, which fasted for 24 hours, to carry out a $^{13}$C-breath test. The rat of 9 weeks old was fixed without anesthesia in a rat holder for a microwave irradiation apparatus. The breath was collected at a rate of about 100 to 300 ml/min using a stroke pump (Variable Stroke Pump VS-500, Shibata Kagaku Kogyo) and introduced directly to a flow cell of a $^{13}$CO$_2$ analyzer EX-130S (Nihon Bunko). A Perma Pure drier (MD-050-12P, Perma Pure INC.) was set between the rat holder and stroke pump to remove out water vapor in the breath. CO$_2$ concentration was stabilized, the rat was once removed out of the rat holder and Bz-DL-Phe-($^{13}$C-Leu).Na dissolved in distilled water was administered into the stomach using an oral sonde.

Output data from the $^{13}$CO$_2$ analyzer were AD converted and put into a personal computer (Apple Power Macintosh 8500). Using a data processing soft ware Lab VIEW (National Instruments), 10 data points at every 100 msec were integrated and averaged in an interval of 5 seconds and converted to $^{13}$C atom %, Δ$^{13}$C (‰), and CO$_2$ concentration (%) In this manner, the $^{13}$C breath test was continuously carried out. The converted data were displayed in real time and stored in a hard disc. CO$_2$ concentration in the collected breath was held at 3±0.5%.

Δ$^{13}$C (‰) was calculated from the $^{13}$C concentration in the exhaled CO$_2$ at each time point ($^{13}$C tmin) and the $^{13}$C concentration in standard CO$_2$ ($^{13}$C std) according to the following equation:

$$\Delta^{13}C\ (‰)=[(^{13}C\ tmin-^{13}C\ 0min)/^{13}C\ std]\times 1000$$

After the breath test, the abdomen of the rat was cut opened under anesthesia by intraperitoneal administration of Nembutal (50 mg/kg) and the whole pancreas was removed and weighed. Then, the chymotrypsinogen content was determined.

15-2 Results

Figure 2:
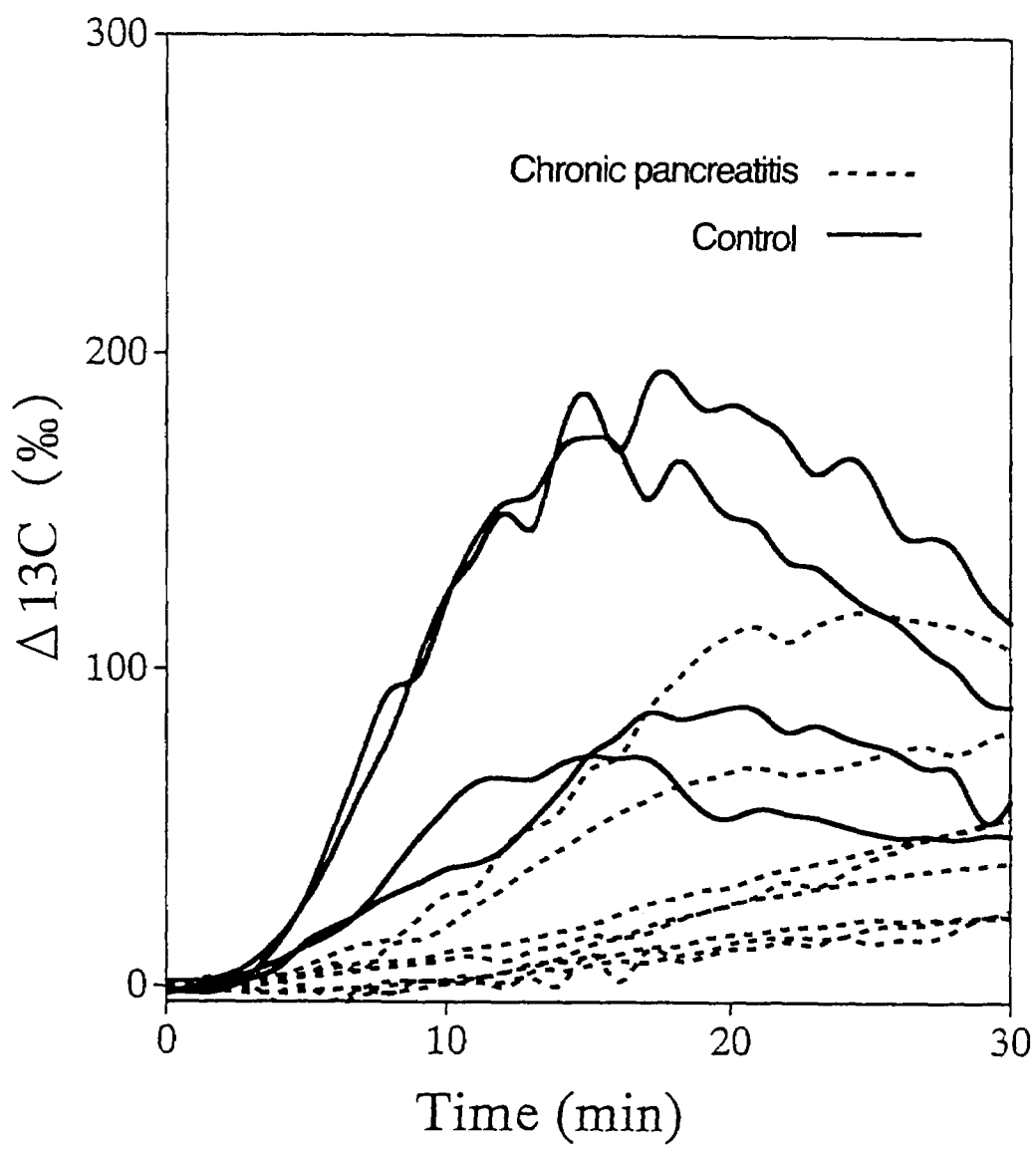
FIG. 2 shows the time course of degree of increase of the $^{13}$C concentration in the exhaled $CO_2$ ($\Delta^{13}$C(‰)) after administration of Bz-DL-Phe-($^{13}$C-Leu)-Na. At 0 minute, Bz-DL-Phe-($^{13}$C-Leu)-Na (250 mg/kg) was orally administered to the chronic pancreatitis rats (dotted line, n=8) and the control rats (solid line, n=4).
Figure 3:
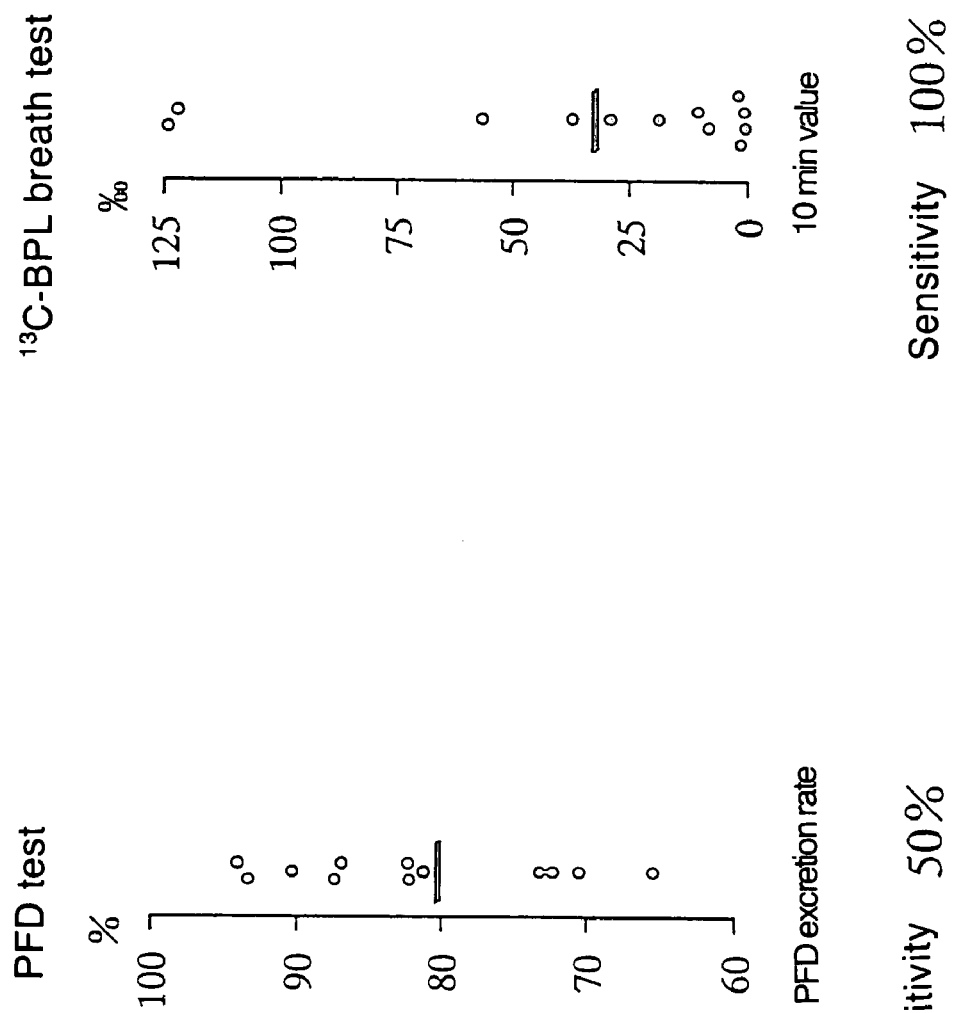
FIG. 3 shows the distribution of values for the chronic pancreatitis rats (○, n=8) and the normal rats (○, n=4) in the PFD and Bz-DL-Phe-($^3$C-Leu) ($^{13}$C-BPL) breath tests. Each rat was subjected to the PFD test prior to the Bz-DL-Phe-($^{13}$C-Leu) breath test. The sensitivity (the ratio of true test positives to total true positives) is shown below for each distribution drawing when a cut off value (bar) is set such that the specificity (the ratio of true test negative to total true negatives) is 100%.

Bz-DL-Phe-($^{13}$C-Leu) breath test was carried out (FIG. 2) wherein 250 mg/kg of Bz-DL-Phe-($^{13}$C-Leu).Na was orally administered to the chronic pancreatitis and control rats and the time course of the $^{13}$CO$_2$ concentration in the exhaled CO$_2$ after the administration was measured. In the control rats, the Δ$^{13}$C (‰) value began to increase at 2 to 3 minutes after the administration, although there was some difference in the degree of increase among individuals. The value reached a peak of 100 to 200‰ at 15 to 20 minutes and then gradually decreased. In 7 cases of the chronic pancreatitis rats, on the contrary, the degree of increase was small and continued to slowly increase for 30 minutes. The remaining one rat showed the same behavior as the control rats but the peak time was later. At 10 minutes after the administration, the Δ$^{13}$C (‰) values of the chronic pancreatitis rats were smaller than the smallest value of Δ$^{13}$C (‰) for the control rats. Accordingly, the sensitivity becomes 100% even when the cut off value is set such that the specificity is made to be 100% by using the Δ$^{13}$C (‰) value at 10 minutes as a check value (FIG. 3). On the other hand, the sensitivity in the PFD test of the same group of rats carried out immediately before the breath test was 50%, indicating that the Bz-DL-Phe-($^{13}$C-Leu) breath test was far superior thereto (FIG. 3). Since it has been reported that the sensivity of simple tests for pancreatic exocrine function other than the PFD test is identical with that of the PFD test, the Bz-DL-Phe-($^{13}$C-Leu) breath test can be said to be the most highly sensitive simple test for pancreatic exocrine function. Further, in addition to the patient's stress because of 6 hours of collecting the urine and forced drinking of a large amount of water, this PFD test is disadvantaged in that subsequent analyses is necessary so that the results are often not found in the same day. On the contrary, the Bz-DL-Phe-($^{13}$C-Leu) breath test has an advantage in that the restraint period is only 10 minutes and that the results can be known soon at that site and time.

Example 16

Bz-Ala-($^{13}$C-Ala) breath test

Figure 4:
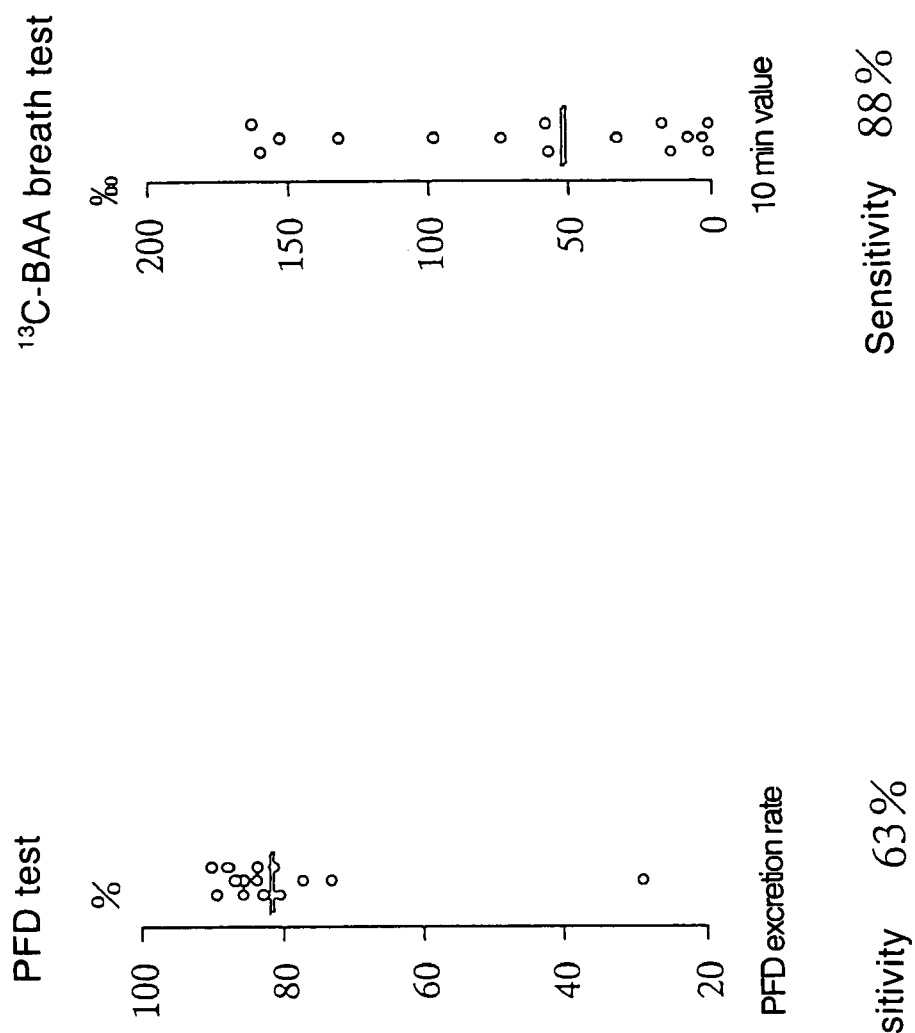
FIG. 4 shows the distribution of values for the chronic pancreatitis rats (○, n=8) and the normal rats (○, n=7) in the PFD and Bz-Ala-($^{13}$C-Ala) ($^{13}$C-BAA) breath tests. Each rat was subjected to the PFD test prior to the Bz-Ala-($^{13}$C-Ala) breath test. The sensitivity (the ratio of true test positives to total true positives) is shown below for each distribution drawing when a cut off value (bar) is set such that the specificity (the ratio of true test negative to total true negatives) is 100%.

In a similar manner to 15-1, Bz-Ala-($^{13}$C-Ala) breath test was carried out wherein 50 mg/kg of Bz-Ala-($^{13}$C-Ala).Na was orally administered and the time course of the $^{13}$CO$_2$ concentration in the exhaled CO$_2$ after the administration was measured. The sensitivity was 88% when the Δ$^{13}$C (‰) value at 10 minutes was used as a check value and a cut off value was set such that the specificity was 100% (FIG. 4). On the other hand, the sensitivity in the PFD test of the same group of rats carried out immediately before the breath test was 63%; thus, the Bz-Ala-($^{13}$C-Ala) breath test was higher in sensitivity (FIG. 4). Further, in addition to the patient's stress due to 6 hours of collecting the urine and forced drinking of a large amount of water, this PFD test is disadvantaged in that subsequent analyses is necessary so that the results are often not found in the same day. On the contrary, the Bz-Ala-($^{13}$C-Ala) breath test could be said to be more excellent in that the restraint period is only 10 minutes and that the results can be known soon at that site and time.

Example 17

Bz-Gly-($^{13}$C-Leu) breath test

In a similar manner to 15-1, Bz-Gly-($^{13}$C-Leu) breath test was carried out wherein 50 mg/kg of Bz-Gly-($^{13}$C-Leu).Na was orally administered and the time course of the $^{13}CO_2$ concentration in the exhaled $CO_2$ after the administration was measured. The sensitivity was 80% when the $\Delta^{13}C$ (‰) value at 18 minutes was used as a check value and a cut off value was set such that the specificity was 100% (FIG. 5). On the other hand, the sensitivity in the PFD test of the same group of rats carried out immediately before the breath test was 50%; thus, the Bz-Gly-($^{13}$C-Leu) breath test was higher in sensitivity (FIG. 5). Further, in addition to the patient's stress due to 6 hours of collecting the urine and forced drinking of a large amount of water, this PFD test is disadvantaged in that subsequent analyses is necessary so that the results are often not found in the same day. On the contrary, the Bz-Gly-($^{13}$C-Leu) breath test has an advantage in that the restraint period is only 18 minutes and that the results can be known soon at that site and time.

Example 18

Preparation of Bz-L-Phe-($^{13}$C-Leu)-OMe

After 3.02 g of 1-$^{13}$C-L-leucine (Masstrace) was dissolved in hydrogen chloride/methanol and refluxed, the resulting $^{13}$C-L-leucine methyl ester was suspended in 150 ml of dichloromethane and 3.22 ml of triethylamine was added dropwise while being ice-cooled and stirred. Further, 6.16 g of N-benzoyl-L-phenylalanine, 7.02 g of HOBt and 100 ml of dichloromethane were added. Then, a solution of 4.4 g of WSC dissolved in 200 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% $NaHCO_3$, and water, dried over magnesium sulfate, and concentrated to dryness to yield 8.36 g of Bz-L-Phe-($^{13}$C-Leu)-OMe.

Example 19

Preparation of Bz-L-Phe-($^{13}$C-Leu) and its Sodium Salt

After 8.36 g of Bz-L-Phe-($^{13}$C-Leu)-OMe was dissolved in 150 ml of methanol, 23.2 ml of 1N NaOH was added dropwise while being ice-cooled and stirred followed by heating and stirring at 70° C. for 3.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% $NaHCO_3$. After washing with ethyl acetate, 5% $NaHCO_3$ was acidified with 1N—HCl. The reaction mixture was extracted with ethyl acetate, washed with water, dried over magnesium sulfate, and concentrated to dryness to yield 7.92 g of Bz-L-Phe-($^{13}$C-Leu), which was then recrystallized with ethyl acetate.

The structure and $^{13}$C-labeled position were confirmed by $^{13}$C-NMR and mass spectrometry.

$^{13}$C-NMR (methanol-d4, 300 MHz): 175.9 ppm ($^{13}$COOH)

Mass spectrometry (m/z): 383 (M$^+$), 365, 224, 131, 105, 77

LC-MS (m/z): 384 (M$^+$+H), 252, 224, 105

The sodium salt of Bz-L-Phe-($^{13}$C-Leu) was obtained by neutralizing Bz-L-Phe-($^{13}$C-Leu) with an equivalent of 1M sodium carbonate followed by lyophilization.

Example 20

Preparation of Bz-Tyr-($^{13}$C-Leu)-OMe

After 1.73 g of 1-$^{13}$C-L-leucine (Masstrace) was dissolved in hydrogen chloride/methanol and refluxed, the resulting $^{13}$C-L-leucine methyl ester was suspended in 100 ml of dichloromethane and 2.00 ml of triethylamine was added dropwise while being ice-cooled and stirred. Further, 4.05 g of N-benzoyl-L-tyrosine, 4.35 g of HOBt and 100 ml of dichloromethane were added. Then, a solution of 2.73 g of WSC dissolved in 150 ml of dichloromethane was added and stirred for 1 hour while being ice-cooled and then overnight at room temperature. The completion of the reaction was confirmed by silica gel thin layer chromatography using chloroform:methanol (95:5) as a developing solvent. The reaction mixture was concentrated, extracted with ethyl acetate, washed with 1N—HCl, 5% $NaHCO_3$, and water, dried over magnesium sulfate, and concentrated to dryness to yield 5.5 g of N-Bz-Tyr-($^{13}$C-Leu)-OMe.

Example 21

Preparation of Bz-Tyr-($^{13}$C-Leu) and its Sodium Salt

After 5.5 g of N-Bz-Tyr-($^{13}$C-Leu)-OMe was dissolved in 150 ml of methanol, 14.6 ml of 1N NaOH was added dropwise while being ice-cooled and stirred followed by heating and stirring at 70° C. for 3.5 hours. The completion of the reaction was confirmed by silica gel thin layer chromatography using chloroform:methanol (95:5) as a developing solvent. After the reaction was completed, the reaction mixture was neutralized with 1N—HCl, concentrated and dissolved in 5% $NaHCO_3$. After washing with ethyl acetate, 5% $NaHCO_3$ was acidified with 1N—HCl. The reaction mixture was extracted with ethyl acetate, washed with water, dried over magnesium sulfate, and concentrated to dryness to yield 4.39 g of N-Bz-Tyr-($^{13}$C-Leu), which was then recrystallized with ethyl acetate.

The structure and $^{13}$C-labeled position were confirmed by $^{13}$C-NMR and mass spectrometry.

$^{13}$C-NMR (methanol-d4, 300 MHz): 175.9 ppm ($^{13}$COOH)

Mass spectrometry (m/z): 399 (M$^+$), 381, 240, 147, 107, 105, 77

LC-MS (m/z): 400 (M$^+$+H), 268, 240

The sodium salt of N-Bz-Tyr-($^{13}$C-Leu) was obtained by neutralizing N-Bz-Tyr-($^{13}$C-Leu) with an equivalent of 1M sodium carbonate followed by lyophilization.

Example 22

Preparation of Arg-($^{13}$C-Leu)

One (1) g of 1-$^{13}$C-L-leucine (Masstrace), 1.7 g of p-toluensulfonic acid monohydrate (TosOH.H$_2$O) and 3.7 ml of benzyl alcohol (BzlOH) were dissolved in 10 ml of dry benzene and heated and refluxed in an oil bath (110° C.) using a Dean-Stark apparatus equipped with a reflux condenser in an evapolation flask the reaction was carried out for 5 hours while separating water produced as the reaction proceeded. After the reaction was over, 15 ml of ether and 15 ml of petroleum ether were added to crystallize the reactant and this was recrystallized with ethanol-ether to yield $^{13}$C-Leu-OBzl.

N α-Carbobenzoxy Ng-tosyl arginine (Z-Arg(Tos)) and an equimolar amount of $^{13}$C-Leu-OBzl were dissolved in dry tetrahydrofuran (THF) and an equimolar amount of HOBt, two molar amounts of dimethylaminopyridine and 1.5 molar amounts of WSC were added to react for 3 hours. After the reaction was over and the solvent was distilled out under reduced pressure, the material was dissolved in chloroform and the chloroform layer was washed sequentially with 10% citric acid, water, 4% NaHCO$_3$ and water. The chloroform layer was dried over Na$_2$SO$_4$ and then the solvent was distilled out. The residue was recrystallized from ethanol-ether to yield Z-Arg(Tos)-$^{13}$C-Leu-OBzl. Then, 1 g of Z-Arg(Tos)-$^{13}$C-Leu-OBzl was dissolved in 3.6 ml of thioanisole, 1.5 ml of trifluoroacetic acid (TFA) and 0.6 ml of trifluoromethyl-sulfonic acid (TFMSA) and reacted at room temperature for 2 hours. After distilling out the solvent, the residue was dissolved in water and treated with an anionic exchange resin (AG-X8, acetic acid type). The resulting solution was concentrated and purified in a LH20 column (2.5 cm×60 cm) equilibrated with methanol: water (1:1) to yield 200 mg of Arg-($^{13}$C-Leu).

The structure and $^{13}$C-labeled position were confirmed by $^1$H-NMR and $^{13}$C-NMR $^1$H-NMR (DMSO-d6, 400 MHz):
  1.073–1.015 ppm 6H: CH—(CH$_3$)$_2$ Leu
  1.868–1.690 ppm 7H: CH—(CH$_3$)$_2$ Leu, CH—CH$_2$—CH Leu CH—CH$_2$—CH$_2$—CH$_2$ Arg
  3.26 ppm 2H: CH$_2$—NH—C=NH$_2$ Arg
  3.477 ppm: H$_2$O
  3.649 ppm $^1$H: NH—CH—COOH Leu
  4.2 ppm $^1$H: NH$_2$—CH—CONH Arg
  7.3–6.8 ppm: guanidine group Arg $^{13}$C-NMR (DMSO-d6, 400 MHz):
  173.3 ppm: NH—CH—($^{13}$C—COOH) Leu

Example 23

Preparation of Phe-($^{13}$C-Leu)

After 9.96 g of 1-$^{13}$C-L-leucine (Masstrace) was dissolved in 75 ml of 1N NaOH, a solution of di-t-butyl dicarbonate (Boc$_2$O) (18.0 g) in acetone (50 ml) was added. Then, 5.21 ml of triethylamine was added dropwise thereto and stirred at room temperature. After one hour, a solution of Boc$_2$O (9.8 g) in acetone (40 ml) was added and stirred overnight at room temperature. After acetone was distilled out under reduced pressure, 500 ml of ethyl acetate was added, precipitated with 6N HCl, washed with water and dried over anhydrous sodium sulfate. After the desicating agent was filtered out, 10 ml of cyclohexylamine (CHA) was added. After washing with 1N HCl, Boc-($^{13}$C-Leu) was extracted with saturated sodium hydrogencarbonate solution and the aqueous layer was acidified with 6N HCl, extracted with ethyl acetate, washed with water and dried over anhydrous sodium sulfate. After concentration under reduced pressure, the residual oily product was dissolved in hexane and 1.2 ml of water was added to crystallize to yield Boc-($^{13}$C-Leu)-OH.H$_2$O. Ten (10) g of Boc-($^{13}$C-Leu)-OH.H$_2$O was dissolved in ethanol (50 ml)-water (20 ml) and 6.52 g of cesium carbonate dissolved in 20 ml of distilled water was added. After concentration under reduced pressure, ethanol and toluene were added and the remaining water was azeotropically removed out to yield a gel product, which was suspended in 300 ml of dimethylformamide (DMF). To the suspension, 5.2 ml of benzyl bromide was dropwise added at room temperature under stirring. After stirring at room temperature for 45 minutes, the solvent was distilled out under reduced pressure. Ethyl acetate was added and washed with water. After drying over anhydrous sodium sulfate, ethyl acetate was distilled out under reduced pressure to yield an oily product. To the product, 59 ml of TFA was added and stirred at room temperature for 40 minutes. After adding 8.37 g of p-toluenesulfonic acid monohydrate, TFA was distilled out under reduced pressure. Diisopropyl ether was added to the residue to crystallize to yield TosOH.H-($^{13}$C-Leu)-OBzl. After dissolving 7.89 g of TosOH.H-($^{13}$C-Leu)-OBzl, 5.57 g of t-Boc-L-phenylalanine (Boc-Phe) and 2.97 g of HOBt in 80 ml of DMF, 4.03 ml of water soluble carbodiimide (WSCD: 1-ethyl-3-(3-dimethylaminopropyl)-carbodiimide) was added dropwise while being ice-cooled and stirred at room temperature for 3 hours. Ethyl acetate and ice water were added and separated into two layers. The organic layer was washed with saturated sodium hydrogen-carbonate, water, 0.1N HCl and water and dried over anhydrous sodium sulfate. After distilling out ethyl acetate under reduced pressure, hexane was added to crystallize to yield Boc-Phe-($^{13}$C-Leu)-OBzl. The Boc-Phe-($^{13}$C-Leu)-OBzl (5.2 g) was dissolved in 10 ml of acetic acid and 500 mg of 5% palladium carbon (Pd—C) was added. While stirring at room temperature, hydrogen gas was blown thereinto for 1 hour. After the catalyst was filtered out, the mother liquid was concentrated under reduced pressure to about 10 ml. While being ice-cooled, 7.23 ml of 4.6N HCl/dioxane was added and stirred for 10 minutes followed by further stirring at room temperature for 1 hour. After concentration under reduced pressure, ether was added to solidify. The resulting solid was filtered out, washed with ether and dissolved in 100 ml of distilled water. The insolubles were filtered off with a membrane filter and lyophilized. This product was purified in RP-HPLC (YMC-ODS (10 μm), 30 mm×250 mm, 20 ml/min, aq. CH$_3$CN (0.05% HCl)) (5%–5%–20%, 0–15–75 minutes) and the main fraction was lyophilized to yield 2.84 g of Phe-($^{13}$C-Leu).

The structure and $^{13}$C-labeled position were confirmed by $^{13}$C-NMR, mass spectrometry and amino acid analysis.

$^{13}$C-NMR (DMSO-d6, 270 MHz): 174.3 ppm ($^{13}$COOH)
MALD-MS (m/z): 280.20 (M$^+$+H)

Amino acid analysis: Phenylalanine 1.00; Leucine 1.01 (hydrolytic conditions: 6N HCl, 110° C., 22 hours)

Example 24

Preparation of Bz-Ala-Ala-Ala-Ala-Gly-Phe-($^{13}$C-Leu) and its Sodium Salt To 33.8 g of N-t-Boc-phenacyl-L-alanine (Boc-Ala-OPac), 9.6 ml of 4.6N HCl/dioxane solution was added and stirred at room temperature for 40 minutes. Diethyl ether was added to solidify and the solid was filtered out and dried under reduced pressure. This material was suspended in 100 ml of dichloromethane and 18.9 g of N-t-Boc-L-alanine (Boc-Ala) was added and cooled to 0° C. After adding 19.2 ml of WSCD, the mixture was stirred at room temperature for 1.5 hours. After concentration under reduced pressure, the residue was dissolved in ethyl acetate/water and the organic layer was washed with water, 1N HCl and water and dried over anhydrous sodium sulfate. Ethyl acetate was distilled out under reduced pressure and diisopropyl ether was added to solidify. The resulting solid was filtered out and recrystallized with acetone-ether-diisopropyl ether to yield Boc-Ala-Ala-OPac.

To 15.1 g of Boc-Ala-Ala-OPac, 88.8 ml of TFA was added and stirred at room temperature for 50 minutes. After concentration under reduced pressure, 11.3 ml of 4.6N HCl/dioxane solution was added. Diethyl ether/diisopropyl ether was added to solidify and the resulting solid was filtered out and dried under reduced pressure. This material was dissolved in 100 ml of DMF and 7.95 g of Boc-Ala and 5.95 g of HOBt were added. After cooling to 0° C. and adding 8.1 ml of WSCD, the mixture was stirred at room temperature for 4 hours. The reaction mixture was cooled and water was added to precipitate. The precipitated solid was filtered out and dissolved in chloroform/methanol (3:1). The organic layer was washed with water and directly concentrated under reduced pressure. Ether was added to crystallize to yield Boc-Ala-Ala-Ala-OPac.

Boc-Ala-Ala-Ala-OPac (8.99 g) was dissolved in 50 ml of dichloromethane/trifluoroethanol (TFE) (3:1) and to this 100 ml of acetic acid was added. Then, 26.2 g of zinc powder was added and vigorously stirred at 35° C. for 1 hour. The insolubles were filtered out and the remaining was concentrated under reduced pressure. Ethyl acetate was added, washed with water and dried over anhydrous sodium sulfate. Ethyl acetate was distilled out under reduced pressure and ether was added to the residue to crystallize to yield Boc-Ala-Ala-Ala-OH.

After 9.96 g of 1-$^{13}$C-L-leucine (Masstrace) was dissolved in 75 ml of 1N NaOH, a solution of Boc$_2$O (18 g) in acetone (50 ml) was added. Then, 5.21 ml of triethylamine was added dropwise thereto and stirred at room temperature. After one hour, a solution of Boc$_2$O (9.8 g) in acetone (40 ml) was added and stirred overnight at room temperature. After acetone was distilled out under reduced pressure, 500 ml of ethyl acetate was added, precipitated with 6N HCl, washed with water and dried over anhydrous sodium sulfate. After the desicating agent was filtered out, 10 ml of CHA was added. After washing with 1N HCl, Boc-($^{13}$C-Leu) was extracted with saturated sodium hydrogencarbonate solution and the aqueous layer was acidified with 6N HCl, extracted with ethyl acetate, washed with water and dried over anhydrous sodium sulfate. After concentration under reduced pressure, the residual oily product was dissolved in hexane and 1.2 ml of water was added to crystallize to yield Boc-($^{13}$C-Leu)-OH.H$_2$O.

Ten (10) g of Boc-($^{13}$C-Leu)-OH.H$_2$O was dissolved in ethanol (50 ml)-water (20 ml) and 6.52 g of cesium carbonate dissolved in 20 ml of distilled water was added. After concentration under reduced pressure, ethanol and toluene were added and the remaining water was azeotropically removed out to yield a gel product, which was suspended in 300 ml of DMF. To the suspension, 5.2 ml of benzyl bromide was added dropwise at room temperature while being stirred. After stirring at room temperature for 45 minutes, the solvent was distilled out under reduced pressure. Ethyl acetate was added and washed with water. After drying over anhydrous sodium sulfate, ethyl acetate was distilled out under reduced pressure to yield an oily product. To the product, 59 ml of TFA was added and stirred at room temperature for 40 minutes. After adding 8.37 g of p-toluenesulfonic acid monohydrate, TFA was distilled out under reduced pressure. Diisopropyl ether was added to the residue to crystallize to yield TosOH.H-($^{13}$C-Leu)-OBzl.

After dissolving 7.89 g of TosOH.H-($^{13}$C-Leu)-OBzl, 5.57 g of Boc-Phe and 2.97 g of HOBt in 80 ml of DMF, 4.03 ml of WSCD was added dropwise while being ice-cooled and the mixture was stirred at room temperature for 3 hours. Ethyl acetate and ice water were added which resulted in two separate layers. The organic layer was washed with saturated sodium hydrogencarbonate, water, 0.1N HCl and water and dried over anhydrous sodium sulfate. After distilling out ethyl acetate under reduced pressure, hexane was added to crystallize to yield Boc-Phe-($^{13}$C-Leu)-OBzl.

To 3.71 g of Boc-Phe-($^{13}$C-Leu)-OBzl, 17.5 ml of TFA was added, stirred at room temperature for 40 minutes and concentrated under reduced pressure. After adding 2.2 ml of 4.6N HCl/dioxane, diisopropyl ether was added to crystallize. The crystal was filtered out, dried under reduced pressure and dissolved in 50 ml of DMF and 2.13 g of Boc-Ala-Gly-OH.H$_2$O and 1.15 g of HOBt were added. While being ice-cooled, 1.56 ml of WSCD was added dropwise, and the mixture was stirred at room temperature for 3 hours. After cooling the reaction mixture, the precipitated solid was filtered out and washed with water. This material was dissolved in ethyl acetate and dried over anhydrous sodium sulfate. After concentration under reduced pressure, the material was crystallized with diisopropyl ether to yield Boc-Ala-Gly-Phe-($^{13}$C-Leu)-OBzl.

To 3.59 g of Boc-Ala-Gly-Phe-($^{13}$C-Leu)-OBzl, 22.2 ml of TFA was added and stirred at room temperature for 45 minutes. After concentration under reduced pressure, 1.7 ml of 4.6N HCl/dioxane was added and solidified with diisopropyl ether. The solid was filtered out and dissolved in 50 ml of DMF and 2.03 g of Boc-Ala-Ala-Ala-OH and 1.06 g of 3-hydroxy-4-oxo-3,4-dihydro-1,2,3-benzotriazine (HOObt) were added. While being ice-cooled 1.19 ml of WSCD was added dropwise and the mixture was stirred at room temperature for 4 hours. After cooling the reaction mixture, water was added and the precipitated solid was filtered out and washed with water. The solid was suspended in methanol, filtered out and dried under reduced pressure. The material was dissolved in 100 ml of chloroform/trifluoroethanol and impurities were filtered out. The solvent was removed out under reduced pressure and ether was added to the residue followed by filtering to yield Boc-Ala-Ala-Ala-Ala-Gly-Phe-($^{13}$C-Leu)-OBzl.

To 2.68 g of Boc-Ala-Ala-Ala-Ala-Gly-Phe-($^{13}$C-Leu)-OBzl, 19 ml of TFA was added and stirred at room temperature for 45 minutes. After concentration under reduced pressure, ether was added to solidify. The solid was filtered out and dissolved in 20 ml of DMF and 0.80 g of benzoyl 1-hydroxysuccinimmide (Bz-ONSu) was added. After adding dropwise 0.5 ml of triethylamine, the mixture was stirred at room temperature for 1 hour. Then, 20 ml of DMF was further added and triethylamine was added to adjust the pH to 6. The mixture was stirred at room temperature for additional 3 hours. After cooling the reaction mixture, water was added and the precipitated solid was filtered out and washed with water. The solid was suspended in methanol and filtered out to yield Bz-Ala-Ala-Ala-Ala-Gly-Phe-($^{13}$C-Leu)-OBzl.

After dissolving 1.63 g of Bz-Ala-Ala-Ala-Ala-Gly-Phe-($^{13}$C-Leu)-OBzl in 80 ml of dichloromethane/hexafluoroisopropyl alcohol (3:1), 0.32 g of 5% palladium-carbon suspended in water/methanol was added. The reaction mixture was stirred at 27° C. for 4 hours while introducing thereinto hydrogen gas. A powdery filter paper was used to filter out the catalyst and the filtrate was concentrated under reduced pressure. Water was added to solidify and the solid was filtered out and washed with water. The solid was suspended in methanol, filtered out and dried under reduced pressure. This material was dissolved in 50 ml of hexafluoroisopropyl alcohol and concentrated under reduced pressure and ethyl acetate was added to the residue to crystallize to yield 1.19 g of Bz-Ala-Ala-Ala-Ala-Gly-Phe-($^{13}$C-Leu).

The structure and $^{13}$C-labeled position were confirmed by $^{13}$C-NMR, mass spectrometry and amino acid analysis.

$^{13}$C-NMR (DMSO-d6, 270 MHz): 173.8 ppm ($^{13}$COOH)

PD-MS (m/z): 725.3 (M$^+$+H), 748.2 (M+Na), 764.4 (M$^+$+K)

Amino acid analysis: Phenylalanine 1.00; Glycine 1.08; Alanine 4.09; Leucine 1.04 (hydrolytic conditions: 6N HCl, 110° C., 22 hours)

The sodium salt of Bz-Ala-Ala-Ala-Ala-Gly-Phe-($^{13}$C-Leu) was obtained by neutralizing Bz-Ala-Ala-Ala-Ala-Gly-Phe-($^{13}$C-Leu) with an equivalent of 1M sodium carbonate followed by lyophilization.

Example 25

Preparation of
Boc-Ala-Ala-Ala-Ala-Gly-Phe-($^{13}$C-Leu) and its
Sodium Salt

As in Example 24, Boc-Ala-Ala-Ala-Ala-Gly-Phe-($^{13}$C-Leu)-OBzl was obtained. After dissolving 1.62 g of Boc-Ala-Ala-Ala-Ala-Gly-Phe-($^{13}$C-Leu)-OBzl in 40 ml of dichloromethane/hexafluoroisopropyl alcohol (3:1), 0.16 g of 5% palladium-carbon suspended in water/methanol was added. Hydrogen gas was introduced into the reaction mixture for 1.5 hours while being stirred at 27° C. A powdery filter paper was used to filter out the catalyst and the filtrate was concentrated under reduced pressure. Acetonitrile was added to solidify and the solid was filtered out. The solid was dried under reduced pressure and dissolved in 30 ml of hexafluoroisopropyl alcohol. The insolubles were filtered out and the remainder was concentrated under reduced pressure. Ethyl acetate was added to the residue and the precipitated gel material was filtered to yield 1.56 g of Boc-Ala-Ala-Ala-Ala-Gly-Phe-($^{13}$C-Leu).

The structure and $^{13}$C-labeled position were confirmed by $^{13}$C-NMR, mass spectrometry and amino acid analysis.

$^{13}$C-NMR (DMSO-d6, 270 MHz): 173.7 ppm ($^{13}$COOH)

PD-MS (m/z): 721.7 (M$^+$+H), 743.9 (M$^+$+Na), 759.9 (M$^+$+K)

Amino acid analysis: Phenylalanine 1.00; Glycine 1.09; Alanine 4.07; Leucine 1.04 (hydrolytic conditions: 6N HCl, 110° C., 22 hours)

The sodium salt of Boc-Ala-Ala-Ala-Ala-Gly-Phe-($^{13}$C-Leu) was obtained by neutralizing Boc-Ala-Ala-Ala-Ala-Gly-Phe-($^{13}$C-Leu) with an equivalent of 1M sodium carbonate followed by lyophilization.

Example 26

Preparation of
Bz-Ala-Ala-Ala-Ala-($^{13}$C-Gly)-Phe-Leu and its
Sodium Salt

After dissolving 5 g of $^{13}$C-glycine (Masstrace) in aqueous solution (17.5 ml) of sodium hydroxide (2.56 g) and adding 3.65 ml of triethylamine, a solution of Boc$_2$O (15.1 ml) in acetone (8 ml) was added and stirred at room temperature for 17 hours. After concentration under reduced pressure, citric acid was added to the aqueous layer to adjust the pH to 4 and sodium chloride was added to salt out followed by extraction with ethyl acetate. The extract was directly dried over magnesium sulfate and the desicating agent was filtered out. After adding 6.76 ml of CHA, the filtrate was allowed to stand overnight in a refrigerator. The precipitated crystal was filtered out to yield Boc-($^{13}$C-Gly)-OH.CHA.

Eight (8) g of Boc-($^{13}$C-Gly)-OH.CHA was suspended in 50 ml of THF and 6.32 ml of 4.6N HCl/dioxane was added. The mixture was fully disrupted in a ultrasonic washer and ether was added. The precipitated solid was filtered out and the filtrate was concentrated under reduced pressure. Ether was added to the residue and the insolubles were filtered and concentrated under reduced pressure. The residue was washed with hexane and filtered out to yield Boc-($^{13}$C-Gly)-OH.

After dissolving 5.31 g of Boc-Phe, 7.87 g of TosOH.H-Leu-OBzl and 2.84 g of HOBt in 40 ml of DMF, 3.72 ml of WSCD was added under ice-cooling and stirred for 30 minutes and at room temperature for further 2.5 hours. After concentration under reduced pressure, ethyl acetate was added, washed sequentially with saturated aqueous sodium hydrogencarbonate solution, saturated aqueous sodium chloride solution, 10% aqueous citric acid solution and saturated aqueous sodium chloride solution, and dried over magnesium sulfate. After concentration under reduced pressure, 43 ml of 4.6N HCl/dioxane was added and allowed to stand at room temperature for 30 minutes. After concentration under reduced pressure, ether was added and the precipitated solid was filtered out to yield HCl.H-Phe-Leu-OBzl.

After dissolving 3.52 g of Boc-($^{13}$C-Gly)-OH, 8.88 g of HCl.H-Phe-Leu-OBzl and 2.70 g of HOBt in 40 ml of DMF, 3.54 ml of WSCD was added under ice-cooling and stirred for 30 minutes and at room temperature for further 14 hours. After concentration under reduced pressure, the material was dissolved in ethyl acetate, washed sequentially with saturated aqueous sodium hydrogencarbonate solution, saturated aqueous sodium chloride solution, 10% aqueous citric acid solution and saturated aqueous sodium chloride solution, and dried over magnesium sulfate. After concentration under reduced pressure, Boc-($^{13}$C-Gly)-Phe-Leu-OBzl was obtained.

To 10.4 g of Boc-($^{13}$C-Gly)-Phe-Leu-OBzl, 42.8 ml of 4.6N HCl/dioxane was added and allowed to stand at room temperature for 45 minutes. After concentration under reduced pressure, an oily product was obtained. The oily product was dissolved in 40 ml of DMF and 3.7 g of Boc-Ala and 2.66 g of HOBt were added followed by adding 3.49 ml of WSCD while being ice-cooled and this was stirred for 30 minutes and for 16 hours further at room temperature. After concentration under reduced pressure, the material was dissolved in ethyl acetate and washed with saturated aqueous sodium hydrogencarbonate solution, saturated aqueous sodium chloride solution, 10% aqueous citric acid solution and saturated aqueous sodium chloride solution. The organic layer was concentrated under reduced pressure and the residue was washed with diisopropyl ether and filtered out to yield Boc-Ala-($^{13}$C-Gly)-Phe-Leu-OBzl.

As in Example 24, Boc-Ala-Ala-Ala-OH was obtained.

To 3.59 g of Boc-Ala-($^{13}$C-Gly)-Phe-Leu-OBzl, 22.2 ml of TFA was added and allowed to stand at room temperature for 45 minutes. After concentration under reduced pressure, 1.7 ml of 4.6N HCl/dioxane was added and diisopropyl ether was added to solidify. The solid was filtered out and dried. This material was dissolved in 50 ml of DMF and 2.03 g of Boc-Ala-Ala-Ala-OH and 1.06 g of HOObt were added. While being ice-cooled 1.19 ml of WSCD was added and this was stirred for 30 minutes and for 14 hours further at room temperature. After cooling the reaction mixture, water was added and the precipitated gel was filtered out to yield Boc-Ala-Ala-Ala-Ala-($^{13}$C-Gly)-Phe-Leu-OBzl.

To a suspension of 2.00 g of Boc-Ala-Ala-Ala-Ala-($^{13}$C-Gly)-Phe-Leu-OBzl and 1.34 ml of anisole, 12 ml of anhydrous hydrogen fluoride was introduced while being stirred and cooled in a dry ice-methanol bath. The material was stirred for 1 hour under cooling at −5° C. and hydrogen fluoride was distilled out at this temperature. Ether was added to the residue and the precipitated solid was filtered out. The solid was suspended into 40 ml of DMF-water (9:1) and 704 mg of Bz-ONSu and 1.03 ml of triethylamine were added and stirred at room temperature for 6 hours. Then, 40 ml of DMF-water (9:1) was added and stirred overnight at room temperature. Further, 541 mg of Bz-ONSu was added and stirred overnight at room temperature. After concentration under reduced pressure, ethyl acetate was added to the residue, fully disrupted in a ultrasonic washer and filtered out to yield 1.53 g of Bz-Ala-Ala-Ala-Ala-($^{13}$C-Gly)-Phe-Leu.

The structure and $^{13}$C-labeled position were confirmed by $^{13}$C-NMR, mass spectrometry and amino acid analysis.

$^{13}$C-NMR (DMSO-d6, 270 MHz): 168.2 ppm ($^{13}$COOH)

PD-MS (m/z): 725.5 (M$^+$+H), 747.8 (M$^+$+Na), 764.3 (M$^+$+K)

Amino acid analysis: Phenylalanine 1.00; Glycine 1.14; Alanine 4.25; Leucine 1.07 (hydrolytic conditions: 6N HCl, 110° C., 22 hours)

The sodium salt of Bz-Ala-Ala-Ala-Ala-($^{13}$C-Gly)-Phe-Leu was obtained by neutralizing Bz-Ala-Ala-Ala-Ala-($^{13}$C-Gly)-Phe-Leu with an equivalent of 1M sodium carbonate followed by lyophilization.

Example 27

Preparation of Bz-Tyr-O-($^{13}$C-Et)

After 5.31 g of N-t-Boc-O-benzyl-L-tyrosine and 3.5 g of 1,2-$^{13}$C-ethanol (Masstrace) were dissolved in 30 ml of DMF, 2.32 g of HOBt was added and 3.14 ml of WSCD was dropwise added under ice-cooling followed by stirring at room temperature for 4 hours. Ethyl acetate was added and the material was washed sequentially with water, saturated aqueous sodium hydrogencarbonate solution, saturated aqueous sodium chloride solution, 1N HCl and saturated aqueous sodium chloride solution, and dried over anhydrous sodium sulfate. The solvent was distilled out under reduced pressure. While cooled at −10° C., 20 ml of TFA was added to the resulting colorless oily product followed by stirring for 10 minutes and for 50 minutes further at room temperature. After concentration under reduced pressure, 3.73 ml of 4.6N HCl/dioxane was added and diisopropyl ether was added to solidify. The residue was filtered out and washed further with diisopropyl ether. This residue was dissolved in 50 ml of DMF and 1.99 ml of benzoyl chloride and 4.00 ml of triethylamine were added while cooled at −10° C. After stirring for 30 minutes and further at room temperature for 3 hours, ethyl acetate was added and washed sequentially with saturated aqueous sodium chloride solution, saturated aqueous sodium hydrogencarbonate solution, saturated aqueous sodium chloride solution, 1N HCl and saturated aqueous sodium chloride solution, and dried over anhydrous sodium sulfate. The solvent was distilled out under reduced pressure and the residue was washed with ether and dried under reduced pressure. This material was recrystallized from methanol to yield Bz-Tyr(Bzl)-O-($^{13}$C-Et). Then, 800 mg of Bz-Tyr(Bzl)-O-($^{13}$C-Et) was dissolved in 30 ml of acetic acid and 1600 mg of palladium black was added. Hydrogen gas was introduced for 6 hours while vigorously stirred at room temperature. Hydrogen gas was stopped and the reaction mixture was stirred overnight at room temperature. A powdery filter paper was used to filter out the catalyst and then acetic acid was distilled out under reduced pressure. Hexane was added and concentration under reduced pressure gave a colorless solid. Water was added and the supernatant was repeatedly removed out by decantation. The material was dissolved in 20% aqueous acetonitrile solution followed by lyophilization. This material was subjected to RP-HPLC (YMC A-323 ODS, 30×250 mm, 20–50% aq. $CH_3CN$ containing 0.1% TFA (60 minutes), flow rate 20 ml/min) to take a main fraction which was then lyophilized to yield 350 mg of Bz-Tyr-O-($^{13}$C-Et).

The structure and $^{13}$C-labeled position were confirmed by $^{13}$C-NMR and mass spectrometry.

$^{13}$C-NMR (CDCl$_3$, 270 MHz): 14.2 ppm ($^{13}$CH$_3$), 61.6 ppm ($^{13}$CH2)

PD-MS (m/z): 316.2 (M$^+$+H)

Example 28

Preparation of Bz-Arg-($^{13}$C-Leu).HCl

As in Example 24, TosOH.H-($^{13}$C-Leu)-OBzl was obtained. After 18.1 g of TosOH.H-($^{13}$C-Leu)-OBzl, 14.5 g of N-t-Boc-arginine hydrochloride monohydrate (Boc-Arg.HCl.H$_2$O) and 5.95 g of HOBt were dissolved in 130 ml of DMF, 8.4 ml of WSCD was added while being cooled at −20° C. and the mixture was stirred at room temperature for 3.5 hours. After DMF was distilled off, the material was dissolved in ethyl acetate and washed with saturated aqueous sodium hydrogencarbonate solution, saturated aqueous sodium chloride solution, 0.1 N HCl and saturated aqueous sodium chloride solution. The material was dried over anhydrous sodium sulfate. After ethyl acetate was distilled off under reduced pressure, hexane was added to yield a crystal. The crystal was filtered out, washed with hexane and dried under reduced pressure. The resultant crude crystal was dissolved in 50 ml of acetonitrile. To this solution, diisopropyl ether was added to yield a crystal of Boc-Arg-($^{13}$C-Leu)-OBzl.TosOH.

To 24.8 g of Boc-Arg-($^{13}$C-Leu)-OBzl.TosOH, 50 ml of TFA was added and the mixture was stirred at room temperature for 30 minutes and concentrated under reduced pressure. After 20 ml of 4.6N HCl/dioxane was added, ether was added to yield a crystal of a hydrochloride. The hydrochloride was filtered out and dried under reduced pressure. To the resultant hydrochloride, 5.12 g of benzoic acid and 5.67 g of HOBt were added and the mixture was dissolved in 110 ml of DMF. To this solution, 7.7 ml of WSCD was added while being cooled at −20° C. and the mixture was stirred at room temperature for 15 hours. The reaction solution was concentrated, dissolved in ethyl acetate and washed with 0.1 N HCl, saturated aqueous sodium chloride solution and saturated aqueous sodium hydrogencarbonate solution to yield a crystal. The crystal was filtered out, washed with ethyl acetate and water, and dissolved in acetic acid. To this solution, ether was added to yield a colorless oily product. The product was dissolved in 250 ml of acetic acid. To this solution, 3 g of palladium-carbon was added. The mixture was stirred at room temperature while introducing hydrogen gas thereinto for 2 hours. The catalyst was filtered off and acetic acid was distilled off. The residue was dissolved in 9 ml of 4.6 N HCl/dioxane. Diisopropyl ether was added to yield a crystal of 16.4 g of Bz-Arg-($^{13}$C-Leu).HCl.

The structure and $^{13}$C-labeled position were confirmed by $^{13}$C-NMR, mass spectrometry and amino acid analysis.

$^{13}$C-NMR (D$_2$O, 270 MHz): 177.5 ppm ($^{13}$COOH)

ESI-MS (m/z): 393.2 (M$^+$+H)

Amino acid analysis: Arginine: 1.00; Leucine 1.02 (hydrolytic conditions: 6N HCl, 110° C., 22 hours)

Example 29

Bz-L-Phe-($^{13}$C-Leu) breath test

As in Example 15-1, Bz-L-Phe-($^{13}$C-Leu) breath test was carried out wherein 250 mg/kg of Bz-L-Phe-($^{13}$C-Leu).Na was orally administered to the chronic pancreatitis rats (n=4) and the normal rats (n=4) and the degree of increase ($^{13}$C (‰)) of the $^{13}$CO$_2$ concentration in the CO$_2$ in the breath after the administration was measured. The $\Delta^{13}$C (‰) value at 10 minutes after the administration was 6.97±6.09‰ in the chronic pancreatitis rats and 115.02±71.26‰ in the normal rats; thus, the value of the chronic pancreatitis rats was significantly smaller than the normal rats (p<0.05 (ANOVA with Fischer LSD)) (Table 1).

TABLE 1

Bz-L-Phe-($^{13}$C-Leu) breath test

|  | $\Delta^{13}$C (‰) at 10 min |
|---|---|
| Chronic pancreatitis #1 | 1.61 |
| Chronic pancreatitis #2 | 3.28 |
| Chronic pancreatitis #3 | 17.21 |
| Chronic pancreatitis #4 | 5.77 |
| Normal #1 | 31.29 |
| Normal #2 | 60.25 |
| Normal #3 | 165.37 |
| Normal #4 | 203.16 |

Bz-L-Phe-($^{13}$C-Leu).Na was orally administered in an amount of 250 mg/kg to the chronic pancreatitis rats (n=4) and the normal rats (n=4).

Example 30

Bz-Tyr-($^{13}$C-Leu) Breath Test

As in Example 15-1, Bz-Tyr-($^{13}$C-Leu) breath test was carried out wherein 250 mg/kg of Bz-Tyr-($^{13}$C-Leu).Na was orally administered to the chronic pancreatitis rats (n=4) and the normal rats (n=4) and the degree of increase ($\Delta^{13}$C (‰)) of the $^{13}$CO$_2$ concentration in the exhaled CO$_2$ after the administration was measured. The $\Delta^{13}$C (‰) value at 20 minutes after the administration was 3.66±3.24‰ in the chronic pancreatitis rats and 69.53±32.50‰ in the normal rats; thus, the value of the chronic pancreatitis rats was significantly smaller than the normal rats (p<0.05 (ANOVA with Fischer LSD)) (Table 2).

TABLE 2

Bz-Tyr-($^{13}$C-Leu) breath test

|  | $\Delta^{13}$C (‰) at 20 min |
|---|---|
| Chronic pancreatitis #1 | 8.76 |
| Chronic pancreatitis #2 | 3.58 |
| Chronic pancreatitis #3 | 2.44 |
| Chronic pancreatitis #4 | −0.15 |
| Normal #1 | 111.32 |
| Normal #2 | 65.76 |
| Normal #3 | 21.02 |
| Normal #4 | 80.02 |

Bz-Tyr-($^{13}$C-Leu).Na was orally administered in an amount of 250 mg/kg to the chronic pancreatitis rats (n=4) and the normal rats (n=4).

Example 31

Arg-($^{13}$C-Leu) Breath Test

As in Example 15-1, Arg-($^{13}$C-Leu) breath test was carried out wherein 30 mg/kg of Arg-($^{13}$C-Leu) was orally administered to the chronic pancreatitis rats (n=4) and the normal rats (n=4) and the degree of increase ($\Delta^{13}$C (‰)) of the $^{13}$CO$_2$ concentration in the exhaled CO$_2$ after the administration was measured. The $\Delta^{13}$C (‰) value at 30 minutes after the administration was 4.37±1.83‰ in the chronic pancreatitis rats and 12.37±2.26‰ in the normal rats; thus, the value of the chronic pancreatitis rats was significantly smaller than the normal rats (p<0.01 (ANOVA with Fischer LSD)) (Table 3).

TABLE 3

Arg-($^{13}$C-Leu) breath test

|  | $\Delta^{13}$C (‰) at 30 min |
|---|---|
| Chronic pancreatitis #1 | 3.74 |
| Chronic pancreatitis #2 | 6.97 |
| Chronic pancreatitis #3 | 4.87 |
| Chronic pancreatitis #4 | 1.92 |
| Normal #1 | 10.30 |
| Normal #2 | 13.74 |
| Normal #3 | 15.37 |
| Normal #4 | 10.08 |

Arg-($^{13}$C-Leu) was orally administered in an amount of 30 mg/kg to the chronic pancreatitis rats (n=4) and the normal rats (n=4).

Example 32

Bz-Ala-Ala-Ala-Ala-($^{13}$C-Gly)-Phe-Leu Breath Test

As in Example 15-1, Bz-Ala-Ala-Ala-Ala-($^{13}$C-Gly)-Phe-Leu breath test was carried out wherein 420 mg/kg of Bz-Ala-Ala-Ala-Ala-($^{13}$C-Gly)-Phe-Leu.Na was orally administered to the chronic pancreatitis rats (n=2) and the normal rats (n=2) and the degree of increase ($\Delta^{13}$C (‰)) of the $^{13}$CO$_2$ concentration in the exhaled CO$_2$ after the administration was measured. The $\Delta^{13}$C (‰) (mean) value at 15 minutes after the administration was 0.61‰ in the chronic pancreatitis rats and 33.32‰ in the normal rats; thus, the value of the chronic pancreatitis rats was smaller than the normal rats (Table 4).

TABLE 4

Bz-Ala-Ala-Ala-Ala-($^{13}$C-Gly)-Phe-Leu breath test

| | $\Delta^{13}$C (‰) at 15 min |
|---|---|
| Chronic pancreatitis #1 | −1.90 |
| Chronic pancreatitis #2 | 3.12 |
| Normal #1 | 23.47 |
| Normal #2 | 43.16 |

Bz-Ala-Ala-Ala-Ala-($^{13}$C-Gly)-Phe-Leu.Na was orally administered in an amount of 420 mg/kg to the chronic pancreatitis rats (n=2) and the normal rats (n=2)

Example 33

Bz-Arg-($^{13}$C-Leu) Breath Test

As in Example 15-1, Bz-Arg-($^{13}$C-Leu) breath test was carried out wherein 100 mg/kg of Bz-Arg-($^{13}$C-Leu).HCl was orally administered to the chronic pancreatitis rats (n=3) and the normal rats (n=3) and the degree of increase ($\Delta^{13}$C (‰)) of the $^{13}CO_2$ concentration in the exhaled $CO_2$ after the administration was measured. The $\Delta^{13}$C (‰) value at 20 minutes after the administration was 3.05±6.97‰ in the chronic pancreatitis rats and 68.77±12.01‰ in the normal rats; thus, the value of the chronic pancreatitis rats was significantly smaller than the normal rats (p<0.01 (ANOVA with Fischer LSD)) (Table 5).

TABLE 5

Bz-Arg-($^{13}$C-Leu) breath test

| | $\Delta^{13}$C (‰) at 20 min |
|---|---|
| Chronic pancreatitis #1 | 3.69 |
| Chronic pancreatitis #2 | 11.25 |

TABLE 5-continued

Bz-Arg-($^{13}$C-Leu) breath test

| | $\Delta^{13}$C (‰) at 20 min |
|---|---|
| Chronic pancreatitis #3 | −5.79 |
| Normal #1 | 51.94 |
| Normal #2 | 74.46 |
| Normal #3 | 79.91 |

Formulation Example 1

Liquid for Internal Use

Purified water was added to 5 parts by weight of Bz-DL-Phe-($^{13}$C-Leu).Na to produce a total of 100 parts by weight and this total amount was dissolved and sterilized through a Millipore filter. The filtrate was taken into a vial bottle and sealed to yield a liquid for internal use.

ADVANTAGES OF THE INVENTION

The present invention provides a highly sensitive pancreatic exocrine function test method which imparts low stress on a subject and gives accurate results soon.

Conventional simple tests for pancreatic exocrine function are less sensitive and therefore have become less used as diagnostic tests for pancreatitis and currently have been utilized generally for follow up of prognosis of pancreatitis which always necessitates repeated tests. However, a highly sensitive simple test for pancreatic exocrine function would be often utilized in diagnosing for pancreatitis in a physical examination. Further, it could be applied to assessing the seriousness of chronic pancreatitis, precognition of onset of serious fulminant pancreatitis with a still high mortality (30%), diagnosis of causes for pancreatitis, and early diagnosis of pancreatic cancer. It would also be usefull as a diagnostic method for ruling out pancreatitis in medical examination of general outpatients.

All publications, patent and patent applications cited herein are incorporated herein by reference in their entirety.

What is claimed is:

1. A $^{13}$C- or $^{14}$C-labeled compound used for measuring pancreatic exocrine function, said compound represented by the following formula (II):

$$X_2-R_2-Y_2-Z_1 \quad (II)$$

or salt thereof, wherein $X_2$ is a benzoyl group, $R_2$ is a peptide of 2 to 5 amino acids, an amino acid or a single bond, $Y_2$ is an amino acid, $Z_1$ is an amino acid optionally having a protecting group, and at least one of the amino acids in $R_2$, $Y_2$, and $Z_1$, or at least one of the protecting groups in $X_2$ and $Z_1$ when the protection groups contain a carbon atom, is $^{13}$C- or $^{14}$C-labeled, wherein in the case where $R_2$ is a single bond, $Z_1$ is D-Ala and $Y_2$ is an amino acid other than D-Ala,
$Z_1$ is L-Ala-OMe and $Y_2$ is an amino acid other than L-Leu, or
$Z_1$ is L-Pro-OMe and $Y_2$ is an amino acid other than L-Gly;

in the case where $R_2$ is an amino acid, $Z_1$ is D-Ala and $Y_2$ is an amino acid other than L-Val,
$Z_1$ is L-Ala and $Y_2$ is an amino acid other than L-Leu, or
$Z_1$ is L-Gly-OEt and $Y_2$ is an amino acid other than L-Pro, or in the case where $R_2$ is a peptide of 2 amino acids, $Z_1$ is L-Gln optionally having SEt, and $Y_2$ is an amino acid other than L-Ala.

2. The $^{13}$C- or $^{14}$C-labeled compound or salt thereof of claim 1, wherein the $^{13}$C- or $^{14}$C-labeled compound is so labeled with $^{13}$C- or $^{14}$C to generate $^{13}$CO$_2$ or $^{14}$CO$_2$ after reacting with a protease or proteases.

3. The $^{13}$C or $^{14}$C-labeled compound or salt thereof of claim 2, wherein the protease or proteases are pancreatic exocrine proteases.

4. The $^{13}$C- or $^{14}$C-labeled compound or salt thereof of claim 3, wherein the pancreatic exocrine protease or proteases are selected from the group consisting of chymotrypsin, trypsin, elastase, and carboxypeptidases.

5. A $^{13}$C- or $^{14}$C-labeled compound used for measuring pancreatic exocrine function, said compound represented by the following formula (II):

$$X_2-R_2-Y_2-Z_1 \quad (II)$$

or salt thereof, wherein $X_2$ is a benzoyl group, $R_2$ is a peptide of 2 to 5 amino acids, an amino acid or a single bond, $Y_2$ is selected from the group consisting of Phe, Ala, Gly, Tyr and Arg, and $Z_1$ is selected from the group consisting of Leu optionally having a protecting group, Ala optionally having a protecting group, and Gly, optionally having a protecting group, and at least one of the amino acids in $R_2$, $Y_2$, and $Z_1$, or at least one of the protecting groups in $X_2$ and $Z_1$ when the protection groups contain a carbon atom, is $^{13}$C- or $^{14}$C-labeled.

6. The $^{13}$C- or $^{14}$C-labeled compound or salt thereof claim 5, wherein $Z_1$ is selected from the group consisting of Leu, Ala, Gly, Leu-OMe, Leu-OEt, Gly-OMe and Gly-OEt.

7. The $^{13}$C- or $^{14}$C-labeled compound or salt thereof of claim 1, wherein $Z_1$ is a $^{13}$C- or $^{14}$C-labeled amino acid optionally having a protecting group.

8. The $^{13}$C- or $^{14}$C-labeled compound or salt thereof of claim 5, which is selected from the group consisting of the following compounds:

Bz-Ala-$^{13}$C-Ala,
Bz-Gly-$^{13}$C-Leu,
Bz-Phe-$^{13}$C-Gly,
Bz-Tyr-$^{13}$C-Leu,
Bz-Phe-$^{13}$C-Leu,
Bz-(DL)Phe-$^{13}$C-Leu,
Bz-Arg-$^{13}$C-Leu,
Bz-Ala-$^{13}$C-Ala-OMe,
Bz-Gly-$^{13}$C-Leu-OMe,
Bz-Phe-$^{13}$C-Gly-OMe,
Bz-Phe-$^{13}$C-Leu-OMe,
BZ-(DL) Phe-$^{13}$C-Leu-OMe,
Bz-Ala-Ala-Ala-Ala-Gly-Phe-$^{13}$C-Leu and
Bz-Ala-Ala-Ala-Ala-$^{13}$C-Gly-Phe-Leu.

9. A $^{13}$C or $^{14}$C-labeled compound used for measuring pancreatic exocrine function, said compound represented by the following formula (IIa)

$$X_{2a}-R_{2a}-Y^{2a}-Z_{1a} \quad (IIa)$$

or a salt thereof, wherein all amino acids constituting the labeled compounds are L-isomers, wherein $X_{2a}$ is a benzoyl group, $R_2$ is a peptide of 2 to 5 amino acids, an amino acid or a single bond, $Y_{2a}$ is an amino acid, $Z_{1a}$ is an amino acid optionally having a protecting group, and at least one of the amino acids in $R_{2a}$, $Y_{2a}$, and $Z_{1a}$ or at least one of the protecting groups in $X_{2a}$ and $Z_{1a}$ when the protecting groups contain a carbon atom, is $^{13}$C- or $^{14}$C-labeled, wherein in the case where $R_{2a}$ is a single bond, $Z_{1a}$ is L-Ala-OMe, and $Y_{2a}$ is an amino acid other than L-Leu; or $R_{2a}$ is a single bond, $Z_{1a}$ is L-Pro-OMe, and $Y_{2a}$ is an amino acid other than L-Gly, in the case where $R_{2a}$ is an amino acid, $Z_{1a}$ is L-Ala, and $Y_{2a}$ is an amino acid other than L-Leu or $Z_{1a}$ is L-Gly-OEt, and $Y_{2a}$ is an amino acid other than L-Pro, or in the case where $R_{2a}$ is a peptide of 2 amino acids $Z_{1a}$ is L-Gln optionally having SEt, and $Y_{2a}$ is an amino acid other than L-Ala.

10. A $^{13}$C or $^{14}$C-labeled compound used for measuring pancreatic exocrine function, said compound represented by the following formula (IIa)

$$X_{2a}—R_{2a}—Y_{2a}—Z_{1a} \quad \text{(IIa)}$$

or a salt thereof, wherein all amino acids constituting the labeled compounds are L-isomers, wherein $X_{2a}$ is a benzoyl group, $R_{2a}$ is a peptide of 2 to 5 amino acids, an amino acid or a single bond, $Y_{2a}$ is selected from the group consisting of L-Phe, L-Ala, L-Gly, L-Tyr and L-Arg, and $Z_{1a}$ is selected from the group consisting of L-Leu optionally having a protecting group, L-Ala optionally having a protecting group, and L-Gly optionally having a protecting group, and at least one of the amino acids in $R_{2a}$, $Y_2$, and $Z_{1a}$ or at least one of the protecting groups in $X_{2a}$ and $Z_{1a}$ when the protecting groups contain a carbon atom, is $^{13}$C- or $^{14}$C-labeled.

11. The $^{13}$C- or $^{14}$C-labeled compound or salt thereof of claim 10, wherein $Z_{1a}$ is selected from the group consisting of L-Leu, L-Ala, L-Gly, L-Leu-OMe, L-Leu-OEt, L-Ala-OMe, L-Ala-OEt, L-Gly-OMe and L-Gly-OEt.

12. The $^{13}$C- or $^{14}$C-labeled compound or salt thereof of claim 9, wherein $Z_{1a}$ is $^{13}$C- or $^{14}$C-labeled amino acid optionally having a protecting group.

13. The $^{13}$C- or $^{14}$C-labeled compound or salt thereof claim 10, which is selected from the group consisting of the following compounds:
Bz-L-Ala-$^{13}$C-L-Ala,
Bz-L-Gly-$^{13}$C-L-Leu,
Bz-L-Phe-$^{13}$C-L-Gly,
Bz-L-Tyr-$^{13}$C-L-Leu,
Bz-L-Phe-$^{13}$C-L-Leu,
Bz-L-Arg-$^{13}$C-L-Leu,
Bz-L-Ala-$^{13}$C-L-Ala-OMe,
Bz-L-Gly-$^{13}$C-L-Leu-OMe,
Bz-L-Phe-$^{13}$C-L-Gly-OMe,
Bz-L-Phe-$^{13}$C-L-Leu-OMe,
Bz-L-Ala-L-Ala-L-Ala-L-Ala-L-Gly-L, -Phe-$^{13}$C-L-Leu, and
Bz-L-Ala-L-Ala-L-Ala-L-Ala-$^{13}$C-L-Gly-L-Phe-L-Leu.

14. A $^{13}$C- or $^{14}$C-labeled compound used for measuring pancreatic exocrine function, said compound represented by the following formula (IIb):

$$X_{2b}—R_{2b}—Y_{2b}—Z_{1b} \quad \text{(IIb)}$$

or a salt thereof, wherein at least one of amino acids constituting the labeled compound is a D-isomer or a DL-mixture,
wherein $X_{2b}$ is a benzoyl group, $R_{2b}$ is a peptide of 2 to 5 amino acids, an amino acid or a single bond, $Y_{2b}$ is an amino acid, $Z_{1b}$ is an amino acid optionally having a protecting group, and at least one of the amino acids in $R_{2b}$, $Y_{2b}$ and $Z_{1b}$, or at least one of the protecting groups in $X_{2b}$ and $Z_{1b}$ when the protecting groups contain a carbon atom, is $^{13}$C- $^{14}$C-labeled,
wherein in the case where $R_{2b}$ is a single bond, $Z_{1b}$ is D-Ala and $Y_{2b}$ is an amino acid other than D-Ala, and in the case where $R_{2b}$ is an amino acid, $Z_{1b}$ is D-Ala and $Y_{2b}$ is an amino acid other then Val.

15. A $^{13}$C- or $^{14}$C-labeled compound used for measuring pancreatic exocrine function, said compound represented by the following formula (IIb):

$$X^{2b}—R^{2b}—Y^{2b}—Z_{1b} \quad \text{(IIb)}$$

or a salt thereof, wherein at least one of amino acids constituting the labeled compound is a D-isomer or a DL-mixture,
wherein $X_{2b}$ is a benzoyl group, $R_{2b}$ is a peptide of 2 to 5 amino acids, an amino acid or a single bond, $Y_{2b}$ is selected from the group consisting of Phe, Ala, Gly, Tyr and Arg, and $Z_{1b}$ is selected from the group consisting of Leu optionally having a protecting group, Ala optionally having a protecting group, and Gly optionally having a protecting group, and at least one of the amino acid $R_{2b}$, $Y_{2b}$ and $Z_{1b}$, or at least one of the protecting groups in $X_{2b}$ and $Z_{1b}$ when the protecting groups contain a carbon atom, is $^{13}$C- $^{14}$C-labeled.

16. The $^{13}$C- or $^{14}$C-labeled compound or salt thereof of claim 15, wherein $Z^{1b}$ is selected from the group consisting of Leu, Ala, Gly, Leu-OMe, Leu-OEt, Ala-OMe, Ala-OEt, Gly-OMe and Glly-OEt.

17. The $^{13}$C or $^{14}$C-labeled compound or salt thereof of claim 14, wherein $Z_{1b}$ is a $^{13}$C- or $^{14}$C-labeled amino acid optionally having a protecting group.

18. The $^{13}$C- or $^{14}$C-labeled compound or salt thereof claim 15, which is selected from the group consisting of the following compounds:
Bz-Ala-$^{13}$C-Ala,
Bz-Gly-$^{13}$C-Leu,
Bz-Phe-$^{13}$C-Gly,
Bz-Tyr-$^{13}$C-Leu,
Bz-Phe-$^{13}$C-Leu,
Bz-(DL)Phe-$^{13}$C-Leu,
Bz-Arg-$^{13}$C-Leu,
Bz-Ala-$^{13}$C-Ala-OMe,
Bz-Gly-$^{13}$C-Leu-OMe,
Bz-Phe-$^{13}$C-Gly-OMe,
Bz-Phe-$^{13}$C-Leu-OMe,
BZ-(DL) Phe-$^{13}$C-Leu-OMe,
Bz-Ala-Ala-Ala-Ala-Gly-Phe-$^{13}$C-Leu and
Bz-Ala-Ala-Ala-Ala-$^{13}$C-Gly-Phe-Leu.

19. A method of measuring pancreatic exocrine function, comprising:
administering a $^{13}$C or $^{14}$C-labeled amino acid or peptide compound, or a pharmaceutically acceptable salt thereof to a subject to be tested for pancreatic exocrine function, the peptide compound or the pharmaceutically acceptable salt thereof comprising 100 amino acids or less; and
measuring a $^{13}$C or $^{14}$C content in an exhaled $CO_2$ of the subject to determine the level of pancreatic exocrine function.

20. The method according to claim 19, wherein the amino acid or peptide compound, or the pharmaceutically acceptable salt thereof is administered orally.

21. The method according to claim 19, wherein the administered $^{13}$C or $^{14}$C-labeled amino acid or peptide compound, or pharmaceutically acceptable salt thereof is decarboxylated to generate $^{13}CO_2$ or $^{14}CO_2$ after a digestion by pancreatic exocrine proteases.

22. The method according to claim 19, wherein the amino acid or each amino acid included in the peptide compound is an L-isomer.

23. The method according to claim 19, wherein the amino acid is a D-isomer or a DL-mixture, or at least one of the amino acids of the peptide compound is a D-isomer or a DL, -mixture.

24. The method according to claim 19, wherein the $^{13}$C or $^{14}$C-labeled peptide compound has two to seven amino acids.

25. The method according to claim 19, wherein the $^{13}$C or $^{14}$C-labeled amino acid or peptide compound, or a pharmaceutically acceptable salt thereof is selected from the group consisting of the following compounds: Bz-L, -Ala-$^{13}$C-L-

Ala, Bz-L-Gly-$^{13}$C-L Leu, Bz-L-Phe-$^{13}$C-L-Gly, Bz-L-Tyr-$^{13}$C-L-Leu, Bz-L-Phe-$^{13}$C-L-Leu, Bz-L-Arg-$^{13}$C-L-Leu, Bz-L-Ala-$^{13}$C-L-Ala-OMe, Bz-L-Gly-$^{13}$C-L-Leu-OMe, Bz-L-Phe-$^{13}$C-L-Gly-OMe, Bz-L, -Phe-$^{13}$C-L-Leu-OMe, Bz-L-Ala-L-Ala-L-Ala-L-Ala-L-Gly-L-Phe-$^{13}$C-L-Leu, and Bz-L-Ala-L-Ala-L-Ala-L-Ala-$^{13}$C-L-Gly-L-Phe-L-Leu.

26. The method according to claim 19, wherein the $^{13}$C or $^{14}$C-labeled amino acid or peptide compound, or a pharmaceutically acceptable salt thereof is selected from the group consisting of the following compounds: Bz-Ala-$^{13}$C-Ala, Bz-Gly-$^{13}$C-Leu, Bz-Phe-$^{13}$C-Gly, Bz-Tyr-$^{13}$C-Leu, Bz-Phe-$^{13}$C-Leu, Bz-(DL)Phe-$^{13}$C-Leu, Bz-Arg-$^{13}$C-Leu, Bz-Ala-$^{13}$C-Ala-OMe, Bz-Gly-$^{13}$C-Leu-OMe, Bz-Phe-$^{13}$C-Gly-OMe, Bz-Phe-$^{13}$C-Leu-OMe, BZ-(DL)Phe-$^{13}$C-Leu-OMe, Bz-Ala-Ala-Ala-Ala-Gly-Phe-$^{13}$C-Leu, and Bz-Ala-Ala-Ala-Ala-$^{13}$C-Gly-Phe-Leu.

27. A method of determining whether a subject has a reduced pancreatic exocrine function, comprising:
  administering a $^{13}$C or $^{14}$C or labeled amino acid or peptide compound, or a pharmaceutically acceptable salt thereof to a subject to be tested for pancreatic exocrine function, the peptide compound or the pharmaceutically acceptable salt thereof comprising 100 amino acids or less,
  measuring a $^{13}$C or $^{14}$C content in an exhaled $CO_2$ of the subject, and
  comparing the $^{13}$C or $^{14}$C content in the exhaled $CO_2$ of the subject to the level of a $^{13}$C or $^{14}$C content in the exhaled $CO_2$ of a healthy control subject who was administered an equivalent amount of the $^{13}$C or $^{14}$C-labeled amino acid or peptide compound or the pharmaceutically acceptable salt thereof,
  wherein the reduced $^{13}$C and $^{14}$C in the exhaled $CO_2$ of the subject is an indication that the subject has a reduced exocrine function.

28. The method according to claim 27, wherein the administration of the amino acid or peptide compound, or the pharmaceutically acceptable salt thereof is conducted orally.

29. The method according to claim 27, wherein the administered $^{13}$C or $^{14}$C-labeled amino acid or peptide compound, or pharmaceutically acceptable salt thereof is decarboxylated to generate $^{13}CO_2$, or $^{14}CO_2$ after a digestion by pancreatic exocrine proteases.

30. The method according to claim 27, wherein the amino acid or each amino acid included in the peptide compound is an L-isomer.

31. The method according to claim 27, wherein the amino acid is a D-isomer or a DL-mixture, or at least one of the amino acids of the peptide compound is a D-isomer or a DL-mixture.

32. The method according to claim 27, wherein the $^{13}$C or $^{14}$C labeled peptide compound has two to seven amino acids.

33. The method according to claim 27, wherein the $^{14}$C or $^{14}$C-labeled amino acid or peptide compound, or a pharmaceutically acceptable salt thereof is selected from the group consisting of the following compounds: -Bz-L-Ala-$^{13}$C-L-Ala, -Bz-L-Gly-$^{13}$C-L-Leu, -Bz-L-Phe-$^{13}$C-L-Gly, -Bz-L-Tyr-$^{13}$C-L-Leu, -Bz-L-Phe-$^{13}$C-L-Leu, -Bz-L-Arg-$^{13}$C-L-Leu, -Bz-L-Ala-$^{13}$C-L-Ala-OMe, -Bz-L-Gly-$^{13}$C-L-Leu-OMe, -Bz-L-Phe-$^{13}$C-L-Gly-ONle, -Bz-L-Phe-$^{13}$C-L-Leu-ONle, -Bz-L-Ala-L-Ala-L-Ala-L-Ala-L-Gly-L-Phe-$^{13}$C-L-Leu, and -Bz-L-Ala-L-Ala-L-Ala-L-Ala-$^{13}$C-L-Gly-L-Phe-L-Leu.

34. The method according to claim 27, wherein the $^{13}$C or $^{14}$C-labeled amino acid or peptide compound, or a pharmaceutically acceptable salt thereof is selected from the group consisting of the following compounds: -Bz-Ala-$^{13}$C-Ala, -Bz-Gly-$^{13}$C-Leu, -Bz-Phe-$^{13}$C-Gly, -Bz-Tyr-$^{13}$C-Leu, -Bz-Phe-$^{13}$C-Leu, -Bz-(DL)Phe-$^{13}$C-Leu, -Bz-Arg-$^{13}$C-Leu, -Bz-Ala-$^{13}$C-Ala-OMe, -Bz-Gly-$^{13}$C-Leu-ONle, -Bz-Phe$^{13}$C-Gly-OMe, -Bz-Phe-$^{13}$C-Leu-OMe, -Bz(DL)Phe-$^{13}$C-Leu-OMe, -Bz-Ala-Ala-Ala-Al-Gly-Phe-$^{13}$C-Leu, and -Bz-Ala-Ala-Ala-Ala-$^{13}$C-Gly-Phe-Leu.

35. A method of determining whether a subject is at risk for pancreatic diseases, comprising: orally administering to a subject a $^{13}$C or $^{14}$C-labeled amino acid or peptide compound, or a pharmaceutically acceptable salt thereof that is digested by pancreatic exocrine proteases, the peptide compound or the pharmaceutically acceptable salt thereof comprising 100 amino acids or less; and determining whether a $^{13}$C or $^{14}$C content in the exhaled $CO_2$ of the subject is lower than the level of a $^{13}$C or $^{14}$C content in the exhaled $CO_2$ of a healthy control subject who was administered an equivalent amount of the $^{13}$C or $^{14}$C-labeled peptide compound or the pharmaceutically acceptable salt thereof, wherein the reduced $^{13}$C and $^{14}$C in the exhaled $CO_2$ of the subject is an indication that the subject is at risk for pancreatic diseases.

36. The method according to claim 35, wherein the pancreatic diseases include chronic or acute pancreatitis and pancreatic cancer.

37. The method according to claim 35, wherein the $^{13}$C or $^{14}$C-labeled amino acid or peptide compound, or the pharmaceutically acceptable salt thereof is decarboxylated to generate $^{13}CO_2$ or $^{14}CO_2$ after a digestion by pancreatic exocrine proteases.

38. The method according to claim 35, wherein the amino acid or each amino acid included in the peptide compound is an L-isomer.

39. The method according to claim 35, wherein the amino acid is a D-isomer or a DL-mixture, or at least one of the amino acids of the peptide compound is a D-isomer or a DL-mixture.

40. The method according to claim 35, wherein the $^{13}$C or $^{14}$C-labeled peptide compound has two to seven amino acids.

41. The method according to claim 35, wherein the $^{13}$C or $^{14}$C-labeled amino acid or peptide compound, or a pharmaceutically acceptable salt thereof is selected from the group consisting of the following compounds: -Bz-Ala-$^{13}$C-Ala, -Bz-Gly-$^{13}$C-Leu, -Bz-Phe-$^{13}$C-Gly, -Bz-Tyr-$^{13}$C-Leu, -Bz-Phe-$^{13}$C-Leu, -Bz-(DL)Phe-$^{13}$C-Leu, -Bz-Arg-$^{13}$C-Leu, Bz-Ala-$^{13}$C-Ala-OMe, -Bz-Gly-$^{13}$C-Leu-OMe-Bz-Phe-$^{13}$C-Gly-OMe, -Bz-Phe-$^{13}$C-Leu-OMe, -Bz-(DL)Phe-$^{13}$C-Leu-OMe, -Bz-Ala-Ala-Ala-Ala-Gly-Phe-$^{13}$C-Leu, and -Bz-Ala-Ala-Ala-Ala-$^{13}$C-Gly-Phe-Leu.

42. The method according to claim 35, wherein the $^{13}$C or $^{14}$C-labeled amino acid or peptide compound, or a pharmaceutically acceptable salt thereof is selected from the group consisting of the following compounds: -Bz-L-Ala-$^{13}$C-L-Ala, -Bz-L-Gly-$^{13}$C-L-Leu, Bz-L-Phe-$^{13}$C-L-Gly, Bz-L-Tyr-$^{13}$C-L-Leu, Bz-L-Phe$^{13}$C-L-Leu, -Bz-L, -Arg-$^{13}$ L-Leu, -Bz-L-Ala-$^{13}$C-L-Ala-OMe, -Bz-L-Gly-$^{13}$C-L-Leu-OMe, -Bz-L-Phe-$^{13}$C-L-Gly-OMe, -Bz-L-Phe-$^{13}$C-L-Leu-OMe, -Bz-L-Ala-L-Ala-L-Ala-L-Ala-L-Gly-L-Phe-$^{13}$C-L-Leu, and -Bz-L-Ala-L-Ala-L-Ala-L-Ala-$^{13}$C-L-Gly-L-Phe-L-Leu.

* * * * *

UNITED STATES PATENT AND TRADEMARK OFFICE
CERTIFICATE OF CORRECTION

PATENT NO. : 7,232,559 B1
APPLICATION NO. : 09/453642
DATED : June 19, 2007
INVENTOR(S) : Kohno et al.

It is certified that error appears in the above-identified patent and that said Letters Patent is hereby corrected as shown below:

In claim 9, col. 52, line 49, "$Y^{2a}$" should read --$Y_{2a}$--.
In claim 9, col. 52, line 53, "$R_2$" should read --R2a--.
In claim 15, col. 53, line 63, "$X^{2b}$-$R^{2b}$-$Y^{2b}$-$Z_{1b}$" should read --$X_{2b}$-$R_{2b}$-$Y_{2b}$-$Z_{1b}$--.
In claim 15, col. 54, line 8, "acid $R_{2b}$" should read --acids in $R_{2b}$--.
In claim 16, col. 54, line 12, "$Z^{1b}$" should read --$Z_{1b}$--.
In claim 16, col. 54, line 14, "Glly-OEt." should read --Gly-OEt.--.
In claim 25, col. 54, line 67, "Bz-L,-Ala-$^{13}$C-L-Ala" should read --Bz-L-Ala-$^{13}$C-L-Ala--.
In claim 25, col. 55, line 4, "Bz-L,-Phe-$^{13}$C-Leu-OMe" should read --BZ-(DL)Phe-$^{13}$C-Leu-OMe--.
In claim 26, col. 55, line 15, "BZ-(DL)Phe-$^{13}$C-Leu-OMe" should read --BZ-(DL)Phe-$^{13}$C-Leu-OMe--.
In claim 33, col. 55, lines 58 - 64, "-Bz" should read --Bz--.
In claim 34, col. 56, lines 4 - 10, "-Bz" should read --Bz--.
In claim 41, col. 56, lines 46 - 52, "-Bz" should read --Bz--.
In claim 42, col. 56, lines 56 - 62, "-Bz" should read --Bz--.
In claim 33, col. 55, line 55, "$^{14}$C" should read --$^{13}$C--.
In claim 33, col. 55, line 62, "ONle" should read --OMe--.
In claim 33, col. 55, line 63, "ONle" should read --OMe--.
In claim 34, col. 56, line 9, "-Bz-Ala-Ala-Ala-Al-Gly-Phe-$^{13}$C-Leu" should read --Bz-Ala-Ala-Ala-Ala-Gly-Phe-$^{13}$C-Leu--.
In claim 41, col. 56, line 49, "-Bz-Gly-$^{13}$C-Leu-OMe-Bz-Phe-$^{13}$C-Gly-OMe" should read --Bz-Gly-$^{13}$C-Leu-OMe-Bz-Phe-$^{13}$C-Gly-OMe--.

UNITED STATES PATENT AND TRADEMARK OFFICE
CERTIFICATE OF CORRECTION

PATENT NO. : 7,232,559 B1
APPLICATION NO. : 09/453642
DATED : June 19, 2007
INVENTOR(S) : Kohno et al.

It is certified that error appears in the above-identified patent and that said Letters Patent is hereby corrected as shown below:

In claim 42, col. 56, line 58, "Bz-L-Phe$^{13}$C-L-Leu" should read
--Bz-L-Phe-$^{13}$C-L-Leu,--.
In claim 42, col. 56, line 58, "-Bz-L,-Arg-$^{13}$L-Leu," should read
--Bz-L-Arg-$^{13}$C-L-Leu,--.

Signed and Sealed this

Twenty-fourth Day of February, 2009

JOHN DOLL
*Acting Director of the United States Patent and Trademark Office*

SEQUENCE LISTING

```
<160> NUMBER OF SEQ ID NOS: 15

<210> SEQ ID NO 1
<211> LENGTH: 4
<212> TYPE: PRT
<213> ORGANISM: Artificial Sequence
<220> FEATURE:
<223> OTHER INFORMATION: Synthetically generated

<400> SEQUENCE: 1

Leu Leu Leu Leu
  1

<210> SEQ ID NO 2
<211> LENGTH: 4
<212> TYPE: PRT
<213> ORGANISM: Artificial Sequence
<220> FEATURE:
<223> OTHER INFORMATION: Synthetically generated
```

```
<400> SEQUENCE: 2

Lys Arg Asp Ser
 1

<210> SEQ ID NO 3
<211> LENGTH: 4
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Acetylation
<221> NAME/KEY: MOD_RES
<222> LOCATION: (4)...(4)
<223> OTHER INFORMATION: Dimethylamino

<400> SEQUENCE: 3

Leu Ala Ala Gln
 1

<210> SEQ ID NO 4
<211> LENGTH: 4
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Acetylation
<221> NAME/KEY: MOD_RES
<222> LOCATION: (4)...(4)
<223> OTHER INFORMATION: Dimethylamino; ethanethiol

<400> SEQUENCE: 4

Leu Ala Ala Gln
 1

<210> SEQ ID NO 5
<211> LENGTH: 5
<212> TYPE: PRT
<213> ORGANISM: Artificial Sequence
<220> FEATURE:
<223> OTHER INFORMATION: Synthetically generated

<400> SEQUENCE: 5

Tyr Gly Gly Phe Leu
 1               5

<210> SEQ ID NO 6
<211> LENGTH: 5
<212> TYPE: PRT
<213> ORGANISM: Artificial Sequence
<220> FEATURE:
<223> OTHER INFORMATION: Synthetically generated

<400> SEQUENCE: 6

Tyr Gly Gly Phe Met
 1               5

<210> SEQ ID NO 7
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Benzoyl
```

```
<221> NAME/KEY: MOD_RES
<222> LOCATION: (7)...(7)
<223> OTHER INFORMATION: labeled with C radioisotope

<400> SEQUENCE: 7

Ala Ala Ala Ala Gly Phe Leu
 1               5

<210> SEQ ID NO 8
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: t-butyloxycarbonyl
<221> NAME/KEY: MOD_RES
<222> LOCATION: (7)...(7)
<223> OTHER INFORMATION: labeled with C radioisotope

<400> SEQUENCE: 8

Ala Ala Ala Ala Gly Phe Leu
 1               5

<210> SEQ ID NO 9
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Benzoyl
<221> NAME/KEY: MOD_RES
<222> LOCATION: (5)...(5)
<223> OTHER INFORMATION: labeled with C radioisotope

<400> SEQUENCE: 9

Ala Ala Ala Ala Gly Phe Leu
 1               5

<210> SEQ ID NO 10
<211> LENGTH: 4
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: t-butyloxycarbonyl
<221> NAME/KEY: MOD_RES
<222> LOCATION: (4)...(4)
<223> OTHER INFORMATION: labeled with C radioisotope
<221> NAME/KEY: MOD_RES
<222> LOCATION: (4)...(4)
<223> OTHER INFORMATION: benzylester

<400> SEQUENCE: 10

Ala Gly Phe Leu
 1

<210> SEQ ID NO 11
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: t-butyloxycarbonyl
```

```
<221> NAME/KEY: MOD_RES
<222> LOCATION: (7)...(7)
<223> OTHER INFORMATION: labeled with C radioisotope
<221> NAME/KEY: MOD_RES
<222> LOCATION: (7)...(7)
<223> OTHER INFORMATION: benzylester

<400> SEQUENCE: 11

Ala Ala Ala Ala Gly Phe Leu
  1               5

<210> SEQ ID NO 12
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Benzoyl
<221> NAME/KEY: MOD_RES
<222> LOCATION: (7)...(7)
<223> OTHER INFORMATION: labeled with C radioisotope; benzylester

<400> SEQUENCE: 12

Ala Ala Ala Ala Gly Phe Leu
  1               5

<210> SEQ ID NO 13
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: Benzoyl
<221> NAME/KEY: MOD_RES
<222> LOCATION: (5)...(5)
<223> OTHER INFORMATION: labeled with C radioisotope

<400> SEQUENCE: 13

Ala Ala Ala Ala Gly Phe Leu
  1               5

<210> SEQ ID NO 14
<211> LENGTH: 7
<212> TYPE: PRT
<213> ORGANISM: Artificial Sequence
<220> FEATURE:
<223> OTHER INFORMATION: Synthetically generated
<221> NAME/KEY: MOD_RES
<222> LOCATION: (1)...(1)
<223> OTHER INFORMATION: t-butyloxycarbonyl
<221> NAME/KEY: MOD_RES
<222> LOCATION: (5)...(5)
<223> OTHER INFORMATION: labeled with C radioisotope
<221> NAME/KEY: MOD_RES
<222> LOCATION: (7)...(7)
<223> OTHER INFORMATION: benzylester

<400> SEQUENCE: 14

Ala Ala Ala Ala Gly Phe Leu
  1               5

<210> SEQ ID NO 15
<211> LENGTH: 7
<212> TYPE: PRT
<213> ORGANISM: Artificial Sequence
<220> FEATURE:
<223> OTHER INFORMATION: Synthetically generated
```

```
<221> NAME/KEY: MOD_RES
<222> LOCATION: (1)...(1)
<223> OTHER INFORMATION: Benzoyl
<221> NAME/KEY: MOD_RES
<222> LOCATION: (5)...(5)
<223> OTHER INFORMATION: labeled with C radioisotope
<221> NAME/KEY: MOD_RES
<222> LOCATION: (7)...(7)
<223> OTHER INFORMATION: sodium salt

<400> SEQUENCE: 15

Ala Ala Ala Ala Gly Phe Leu
 1               5
```